US012714367B2

(12) United States Patent
Stuart et al.

(10) Patent No.: US 12,714,367 B2
(45) Date of Patent: Aug. 25, 2026

(54) THREE-DIMENSIONAL PRINTED ARTICLES AND METHODS OF MANUFACTURE

(71) Applicant: ARIZONA BOARD OF REGENTS ON BEHALF OF THE UNIVERSITY OF ARIZONA, Tucson, AZ (US)

(72) Inventors: Tucker Stuart, Tucson, AZ (US); Philipp Gutruf, Tucson, AZ (US)

(73) Assignee: Arizona Board of Regents On Behalf of The University of Arizona, Tucson, AZ (US)

( * ) Notice: Subject to any disclaimer, the term of this patent is extended or adjusted under 35 U.S.C. 154(b) by 197 days.

(21) Appl. No.: 18/281,527

(22) PCT Filed: Mar. 11, 2022

(86) PCT No.: PCT/US2022/020030

§ 371 (c)(1),
(2) Date: Sep. 11, 2023

(87) PCT Pub. No.: WO2022/192723

PCT Pub. Date: Sep. 15, 2022

(65) Prior Publication Data

US 2024/0164717 A1 May 23, 2024

Related U.S. Application Data

(60) Provisional application No. 63/159,884, filed on Mar. 11, 2021.

(51) Int. Cl.

| | |
|---|---|
| ***A61B 5/00*** | (2006.01) |
| ***A61B 5/01*** | (2006.01) |

(Continued)

(52) U.S. Cl.

CPC .............. *A61B 5/6831* (2013.01); *A61B 5/01* (2013.01); *A61B 5/6802* (2013.01); *B33Y 10/00* (2014.12);

(Continued)

(58) Field of Classification Search

CPC ....... A61B 5/68; A61B 5/6801; A61B 5/6813; A61B 5/6824; A61B 5/683; A61B 5/6831;

(Continued)

(56) References Cited

U.S. PATENT DOCUMENTS

| | | | |
|---|---|---|---|
| 8,140,143 | B2 | 3/2012 | Picard et al. |
| 11,065,439 | B1 | 7/2021 | Halpern |

(Continued)

FOREIGN PATENT DOCUMENTS

| | | | |
|---|---|---|---|
| WO | 2022192723 | A1 | 9/2022 |
| WO | 2023055864 | A1 | 4/2023 |

OTHER PUBLICATIONS

International Search Report and Written Opinion from corresponding PCT Appln. No. PCT/US2022/020030, dated Jul. 15, 2022. 4 pages.

(Continued)

*Primary Examiner* — Benjamin R Schmitt

(74) *Attorney, Agent, or Firm* — Secant IP, PLLC; Edmund P. Pfleger

(57) ABSTRACT

Three-dimensionally (3D) printed, wearable, electronic sensing articles and methods of manufacture are disclosed. In one example embodiment, the present disclosure provides A wearable article that includes a three-dimensionally printed base, wherein the base of the article comprises a three-dimensionally printed mesh which is formed of an elastomeric polymer composition. The wearable article also includes a microfluidic channel coupled to the mesh, the (Continued)

microfluidic channel having an inlet and an outlet disposed at opposite ends of the channel, wherein the microfluidic channel is curved in a form of a serpentine shape; and wherein the serpentine shape is provided by a plurality of 180-degree semi-circular segments.

21 Claims, 24 Drawing Sheets

(51) Int. Cl.

| | |
|---|---|
| ***B33Y 10/00*** | (2015.01) |
| ***B33Y 80/00*** | (2015.01) |
| ***B81B 7/00*** | (2006.01) |
| *B29C 64/118* | (2017.01) |
| *B33Y 70/00* | (2020.01) |
| *G01D 11/30* | (2006.01) |

(52) U.S. Cl.

CPC ............ *B33Y 80/00* (2014.12); *B81B 7/0061* (2013.01); *A61B 5/4266* (2013.01); *A61B 2562/12* (2013.01); *B29C 64/118* (2017.08); *B33Y 70/00* (2014.12); *B81B 2201/058* (2013.01); *G01D 11/30* (2013.01)

(58) Field of Classification Search

CPC ....... A61B 5/01; A61B 5/6802; A61B 5/4266; A61B 2562/12; B33Y 80/00; B33Y 10/00; B33Y 70/00; B81B 2201/058; G01D 11/30

See application file for complete search history.

(56) References Cited

U.S. PATENT DOCUMENTS

| | | | | |
|---|---|---|---|---|
| 2003/0014091 | A1 | 1/2003 | Rastegar et al. | |
| 2008/0200774 | A1 | 8/2008 | Lou | |
| 2010/0019832 | A1 | 1/2010 | Pan | |
| 2013/0041235 | A1 | 2/2013 | Rogers | |
| 2014/0347845 | A1 | 11/2014 | Pulido | |
| 2015/0148619 | A1 | 5/2015 | Berg et al. | |
| 2016/0006123 | A1 | 1/2016 | Li et al. | |
| 2017/0165908 | A1 | 6/2017 | Pattinson et al. | |
| 2017/0181659 | A1 | 6/2017 | Rafferty et al. | |
| 2018/0064377 | A1 | 3/2018 | Rogers et al. | |
| 2018/0223090 | A1 | 8/2018 | Abusleme et al. | |
| 2018/0241218 | A1 | 8/2018 | Spinella | |
| 2018/0271393 | A1 | 9/2018 | Lee et al. | |
| 2018/0376235 | A1 | 12/2018 | Laebman et al. | |
| 2019/0069788 | A1 | 3/2019 | Coleman et al. | |
| 2019/0090801 | A1 | 3/2019 | Rogers et al. | |
| 2019/0191703 | A1 | 6/2019 | Day et al. | |
| 2019/0344080 | A1 | 11/2019 | McDonald et al. | |
| 2019/0353533 | A1 | 11/2019 | Marchesi | |
| 2020/0008299 | A1 | 1/2020 | Tran et al. | |
| 2020/0129077 | A1 | 4/2020 | Rogers et al. | |
| 2020/0186179 | A1 | 6/2020 | Horiuchi | |
| 2020/0188180 | A1* | 6/2020 | Akbari | A61F 13/0213 |
| 2020/0238604 | A1* | 7/2020 | Hart | A61F 2/0063 |
| 2020/0391021 | A1 | 12/2020 | Sachs et al. | |
| 2021/0022686 | A1 | 1/2021 | Rogers | |
| 2021/0145352 | A1 | 5/2021 | Rogers et al. | |
| 2021/0386300 | A1 | 12/2021 | Rogers et al. | |
| 2022/0062651 | A1 | 3/2022 | Yeh | |
| 2022/0233124 | A1 | 7/2022 | Connor | |

OTHER PUBLICATIONS

International Preliminary Report on Patentability from corresponding PCT Appln. No. PCT/US2022/020030, dated Sep. 12, 2023. 7 pages.

Matsuhisa, N. et al., Printable elastic conductors with a high conductivity for electronic textile applications. Nat Commun 6, (2015).

Abot, J. L., Alosh, T. & Belay, K., Strain dependence of electrical resistance in carbon nanotube yarns. Carbon N Y 70, 95-102 (2014).

Hashemi Sanatgar, R. et al., Piezoresistive Properties of 3D-Printed Polylactic Acid (PLA) Nanocomposites. Polymers (Basel) 14, (2022).

Oliva-Avilés, A. I., Avilés, F., Seidel, G. D. & Sosa, V., On the contribution of carbon nanotube deformation to piezoresistivity of carbon nanotube/polymer composites. Compos B Eng 47, 200-206 (2013).

Kordas, K. & Pitkänen, O., Piezoresistive carbon foams in sensing applications. Front Mater 6, (2019).

Yang, L. et al., Insight into the Contact Impedance between the Electrode and the Skin Surface for Electrophysical Recordings. ACS Omega 7, 13906-13912 (2022).

Elango, P. F. M. et al., Dry electrode geometry optimization for wearable ECG devices. Appl Phys Rev 10, (2023).

Ashley, E. A. & Niebauer, Josef, Cardiology Explained. (Remedica, 2004).

Berkebile, John A. et al., Towards Estimation of Tidal vol. and Respiratory Timings via Wearable-Patch-Based Impedance Pneumography in Ambulatory Settings, IEEE Transaction on Biomedical Engineering, vol. 89, No. 6. Jun. 2022.

Cömert, A., Honkala, M. & Hyttinen, J., Effect of Pressure and Padding on Motion Artifact of Textile Electrodes. http://www.biomedical-engineering-online.com/content/12/1/26 (2013).

Smital, L. et al., Real-Time Quality Assessment of Long-Term ECG Signals Recorded by Wearables in Free-Living Conditions. IEEE Trans Biomed Eng 67, 2721-2734 (2020).

Black, N. et al., Circadian rhythm of cardiac electrophysiology, arrhythmogenesis, and the underlying mechanisms. Heart Rhythm 16, 298-307 (2019).

Barrett, P. M. et al., Comparison of 24-hour Holter monitoring with 14-day novel adhesive patch electrocardiogramonitoring. American Journal of Medicine 127, 95.e11-95.e17 (2014).

Cormie, P., Mcguigan, M. R. & Newton, R. U., Developing Maximal Neuromuscular Power Part 1—Biological Basis of Maximal Power Production.

Mason, J. et al., Determining the early corticospinal-motoneuronal responses to strength training: A systematic review and meta-analysis. Rev Neurosci 30, 463-476 (2019).

ASTM Standard, Standard Test Method for Peel Resistance of Adhesives (T-Peel Test) C1876-08, 2015, 15.06.

Arquilla, Kalya et al., Wearable 3-Lead Electrocardiogram Placement Model for Fleet Sizing of Medical Devices, Aerospace Medicine and Human Performance, vol. 91, No. 11, Nov. 2020, pp. 868-875.

Pasadyn, S. R. et al., Accuracy of commercially available heart rate monitors in athletes: A prospective study. Cardiovasc Diagn Ther 9, 379-385 (2019).

Clausen, D. et al., Chronic Biosymbiotic Electrophysiology, Advanced Functional Materials, 2025, 35, 2407086.

International Search Report and Written Opinion of International Application No. PCT/US24/28943, mail date Oct. 21, 2024, 16 pages.

Wagih et al., Dual-Polarized Wearable Antenna/Rectenna for Full-Duplex and MIMO Simultaneous Wireless Information and Power Transfer (SWIPT), IEE Open Journal of Antennas and Propagation, Aug. 2, 2021.

Stuart, Biosymbiotic Wearable Devices: A Personalized and Digitally Manufactured Platform for Continuous Collection of High-Fidelity Biosignals, 2023.

International Preliminary Report on Patentability of International Application No. PCT/US24/028943, issued Nov. 13, 2025, 13 pages.

A. Atreja et al., Digital medicine and evolution of remote patient monitoring in cardiac electrophysiology: a state-of-the-art perspective. Curr. Treat. Options Cardiovasc. Med. 21, 1-10 (2019).

B. Noah, et al., Impact of remote patient monitoring on clinical outcomes: an updated meta-analysis of randomized controlled trials. NPJ Digit. Med. 1, 20172 (2018).

(56) References Cited

OTHER PUBLICATIONS

A. Vegesna, Remote patient monitoring via non- invasive digital technologies: a systematic review. Telemed. e-Health 23, 3-17 (2017).
T. Annis, et al., Rapid implementation of a COVID-19 remote patient monitoring program. J. Am. Med. Informatics Assoc. 27, 1326-1330 (2020).
O. Taiwo, et al., Smart healthcare support for remote patient monitoring during covid-19 quarantine. Informatics Med. unlocked 20, 100428 (2020).
D. R. Seshadri, et al., Wearable sensors for COVID-19: a call to action to harness our digital infrastructure for remote patient monitoring and virtual assessments. Front. Digit. Heal., 8 (2020).
L. Garg, et al., Anonymity preserving IoT-based COVID-19 and other infectious disease contact tracing model. Ieee Access 8, 159402-159414 (2020).
M. Haghi Kashani, et al., A systematic review of IoT in healthcare: Applications, techniques, and trends. J. Netw. Comput. Appl. 192, 103164 (2021).
T. Stuart, et al., Wearable devices for continuous monitoring of biosignals: Challenges and opportunities. APL Bioeng. 6, 021502 (2022).
T. Stuart, et al., Wireless and battery-free platforms for collection of biosignals. Biosens. Bioelectron. 178, 113007 (2021).
S. Sharma, et al., Issues and challenges in wireless sensor networks in 2013 International Conference on Machine Intelligence and Research Advancement, (IEEE, 2013), pp. 58-62.
C. F. Garcia-Hernandez, et al., Wireless sensor networks and applications: a survey. IJCSNS Int. J. Comput. Sci. Netw. Secur. 7, 264-273 (2007).
M. A. Matin, et al., Overview of wireless sensor network. Wirel. Sens. networks-technology Protoc. 1 (2012).
M. De Sanctis, et al., Satellite communications supporting internet of remote things. IEEE Internet Things J. 3, 113-123 (2015).
S. Nazir, et al., WiSE—a satellite-based system for remote monitoring. Int. J. Satell. Commun. Netw. 35, 201-214 (2017).
H.-B. Li, et al., Wireless body area network combined with satellite communication for remote medical and healthcare applications. Wirel. Pers. Commun. 51 pp. 697-709 (2009).
F. Adelantado, et al., Understanding the limits of LoRaWAN. IEEE Commun. Mag. 55, 34-40 (2017).
S. Hariprasad, et al., Improving Unwavering Quality and Adaptability Analysis of LoRaWAN. Procedia Comput. Sci. 171, 2334-2342 (2020).
A. Alsaraira, et al., Design of LoRa Antenna for Wearable Medical Applications. IEEE Access 11, 23886-23895 (2023).
Y. Jain, et al., Novel wearable device for health monitoring and tracking of soldiers based on LoRa module in 2020 IEEE 4th Conference on Information & Communication Technology (CICT), (IEEE, 2020), pp. 1-5.
G. B. Tayeh, et al., A wearable lora-based emergency system for remote safety monitoring in 2020 International Wireless Communications and Mobile Computing (IWCMC), (IEEE, 2020), pp. 120-125.
R. M. Aileni, et al., "Internet of wearable low-power wide-area network devices for health self-monitoring" in LPWAN Technologies for IoT and M2M Applications, (Elsevier, 2020), pp. 307-325.
N. W. Wilson, et al., A critical review of interventions to redress the inequitable distribution of healthcare professionals to rural and remote areas. Rural Remote Health 9, 1-21 (2009).
D. Padeken, et al., Health care in remote areas. J. Med. Syst. 19, 69-76 (1995).
W. H. Organization, Medical devices and eHealth solutions: Compendium of innovative health technologies for low-resource settings 2011-2012 (World Health Organization, 2013).
N. V. V. Chau, et al., Wearable remote monitoring for patients with COVID-19 in low-resource settings: case study. BMJ Innov. 7 pp. s12-s15 (2021).
T. Stuart, et al., Context-aware electromagnetic design for continuously wearable biosymbiotic devices. Biosens. Bioelectron. (2023) https:/doi.org/10.1016/j.bios.2023.115218.
Krishnan, S. R. et al. Wireless, Battery-Free Epidermal Electronics for Continuous, Quantitative, Multimodal Thermal Characterization of Skin. Small 14, 1803192 (2018).
Kim, J. et al. Miniaturized Battery-Free Wireless Systems for Wearable Pulse Oximetry. Adv Funct Mater 27, 1604373 (2017).
Kim, J. et al. Miniaturized Flexible Electronic Systems with Wireless Power and NearField Communication Capabilities. Adv Funct Mater 25, 4761-4767 (2015).
Rahman, M. A. et al. Nicotine Sensors for Wearable Battery-Free Monitoring of Vaping. ACS Sens 7, 82-88 (2022).
Yu, X. et al. Skin-integrated wireless haptic interfaces for virtual and augmented reality. Nature 575, 473-479 (2019).
Yedavalli, P. S., Riihonen, T., Wang, X. & Rabaey, J. M. Far-field RF wireless power transfer with blind adaptive beamforming for Internet of Things devices. IEEE Access 5, 1743-1752 (2017).
Xia, M. & Aissa, S. On the efficiency of far-field wireless power transfer. IEEE transactions on signal processing 63, 2835-2847 (2015).
Dobkin, D. M. The rf in RFID: uhf RFID in practice. (Newnes, 2012).
Shuai, K., Yang, J., Liu, C., Yang, X. & Liu, X. Beam-steering transmitarray with active frequency selective surface for wireless power transmission. International Journal of RF and Microwave Computer-Aided Engineering 31, e22907 (2021).
Lee, K., Kim, J. & Cha, C. Microwave-based wireless power transfer using beam scanning for wireless sensors. in IEEE EUROCON 2019—18th International Conference on Smart Technologies 1-5 (IEEE, 2019).
Eid, A. M. et al. A novel high power frequency beam-steering antenna array for longrange wireless power transfer. Alexandria Engineering Journal 60, 2707-2714 (2021).
Tong, H. & Geyi, W. Optimal design of smart antenna systems for handheld devices. IET Microwaves, Antennas & Propagation 10, 617-623 (2016).
Sun, C., Cheng, J. & Ohira, T. Handbook on advancements in smart antenna technologies for wireless networks. (IGI Global, 2008).
Wei, K. & Kording, K. P. Behavioral tracking gets real. Nat Neurosci 21, 1146-1147 (2018).
Mathis, A. et al. DeepLabCut: markerless pose estimation of user-defined body parts with deep learning. Nat Neurosci 21, 1281-1289 (2018).
Pollard, B., Mcdonald, G., Held, F. & Engelen, L. Stop motion: using high resolution spatiotemporal data to estimate and locate stationary and movement behaviour in an office workplace. Ergonomics 65, 675-690 (2022).
Sun, J. et al. Highly stretchable and ultrathin nanopaper composites for epidermal strain sensors. Nanotechnology 29, 355304 (2018).
Ledger, D. & Mccaffrey, D. Inside wearables: How the science of human behavior change offers the secret to long-term engagement. Endeavour Partners 200, 1 (2014).
Lazar, A., Koehler, C., Tanenbaum, T. J. & Nguyen, D. H. Why we use and abandon smart devices. in Proceedings of the 2015 ACM international joint conference on pervasive and ubiquitous computing 635-646 (2015).
Maher, C., Ryan, J., Ambrosi, C. & Edney, S. Users' experiences of wearable activity trackers: a cross-sectional study. BMC Public Health 17, 1-8 (2017).
Elleuch, R., Elleuch, K., Salah, B. & Zahouani, H. Tribological behavior of thermoplastic polyurethane elastomers. Mater Des 28, 824-830 (2007).
Yang, C., Vora, H. D. & Chang, Y. Behavior of auxetic structures under compression and impact forces. Smart Mater Struct 27, (2018).
Nath, T. et al. Using DeepLabCut for 3D markerless pose estimation across species and behaviors. Nat Protoc 14, 2152-2176 (2019).
International Search Report and Written Opinion of International Application No. PCT/US22/20030, mail date Jul. 15, 2022, 11 pages.
International Preliminary Report on Patentability of International Application No. PCT/US22/20030, issued Sep. 12, 2023, 7 pages.

(56) References Cited

OTHER PUBLICATIONS

Stuart, et al., "Context-Aware Eelctromagnetic Design for Continuously Wearable Biosymbiotic Devices", Biosensors and Bioelectronics, vol. 228, https://www.sciencedirect.com/science/article/pii/S0956566323001604, Elsevier, May 15, 2023, pp. 1-23.
NSF Award Search: Award # 1608289—In Operando Characterization of Degradation Processes in Organic Semiconductor Materials, https://www.nsf.gov/awardsearch/showAward?AWD_ID=1608289, Division of Materials Research, 2016, pp. 1-7.
NonFinal Office Action of U.S. Appl. No. 18/281,527, mail date Aug. 26, 2025, 22 pages.
International Search Report and Written Opinion of International Application No. PCT/US2025/025921, mail date Aug. 20, 2025, 16 pages.
Yildirim, Ö., Pławiak, P., Tan, R. S. & Acharya, U. R., Arrhythmia detection using deep convolutional neural network with long duration ECG signals. Comput Biol Med 102, 411-420 (2018).
Aziz, S., Ahmed, S. & Alouini, M. S., ECG-based machine-learning algorithms for heartbeat classification. Sci Rep 11, (2021).
Kim, H. et al., Skin preparation-free, stretchable microneedle adhesive patches for reliable electrophysiological sensing and exoskeleton robot control. Sci Adv 10, (2024).
Ravichandran, V., Ciesielska-Wrobel, I., Rumon, M. A. Al, Solanki, D. & Mankodiya, K., Characterizing the Impedance Properties of Dry E-Textile Electrodes Based on Contact Force and Perspiration. Biosensors (Basel) 13, (2023).
Machino, T. et al., Randomized crossover trial of 2-week Garment electrocardiogram with dry textile electrode to reveal instances of post-ablation recurrence of atrial fibrillation underdiagnosed during 24-hour Holter monitoring. PLoS One 18, (2023).
Seshadri, D. R., Radwan, A. N., Bianco, N. D., Zorman, C. A. & Bogie, K. M., Flexible and Scalable Dry Conductive Elastomeric Nanocomposites for Surface Stimulation Applications. IEEE Trans Biomed Eng 70, 3461-3468 (2023).
Carrington, M. et al., Monitoring and diagnosis of intermittent arrhythmias: evidence-based guidance and role of novel monitoring strategies. European Heart Journal Open vol. 2 Preprint at https://doi.org/10.1093/ehjopen/oeac072 (2022).
Grimnes, S. & Martinsen, Ø. G., Selected Applications. in Bioimpedance and Bioelectricity Basics 405-494 (Elsevier, 2015). doi:10.1016/b978-0-12-411470-8.00010-6.
Seppä, V. P. et al., Tidal flow variability measured by impedance pneumography relates to childhood asthma risk. European Respiratory Journal 47, 1687-1696 (2016).
Berkebile, J. A. et al., Towards Estimation of Tidal Volume and Respiratory Timings via Wearable-Patch-Based Impedance Pneumography in Ambulatory Settings. IEEE Trans Biomed Eng 69, 1909-1919 (2022).
Kapur, S., Sweeney, M. O., Sauer, W. & Macrae, C. A., Non-invasive Thoracic Impedance Changes in COVID-19 Pulmonary Infection. J Cardiovasc Transl Res 14, 387-389 (2021).
Moeyersons, J. et al., Artefact detection in impedance pneumography signals: A machine learning approach. Sensors 21, (2021).
Tuohimäki, K. et al., Electrode comparison for textile-integrated electrocardiogram and impedance pneumography measurement. in IFMBE Proceedings vol. 65 302-305 (Springer Verlag, 2017).
IEEE Engineering in Medicine and Biology Society. Annual International Conference of the IEEE Engineering in Medicine and Biology Society (EMBC), 2012 San Diego, California, USA, Aug. 28-Sep. 1, 2012.
Dheman, K., Mayer, P., Eggimann, M., Schuerle, S. & Magno, M., ImpediSense:A long lasting wireless wearable bio-impedance sensor node. Sustainable Computing: Informatics and Systems 30, (2021).
Rodríguez-Rodríguez, F., Cristi-Montero, C., González-Ruíz, K., Correa-Bautista, J. E. & Ramírez-Vélez, R., Bioelectrical impedance vector analysis and muscular fitness in healthy men. Nutrients 8, (2016).
Ngo, C. et al., A Wearable, Multi-Frequency Device to Measure Muscle Activity Combining Simultaneous Electromyography and Electrical Impedance Myography. Sensors 22, (2022).
Kusche, R., Oltmann, A. & Rostalski, P., A Wearable Dual-Channel Bioimpedance Spectrometer for Real-Time Muscle Contraction Detection. IEEE Sens J (2024) doi: 10.1109/JSEN.2024.3359284.
Vidhya, C. M., Maithani, Y. & Singh, J. P., Recent Advances and Challenges in Textile Electrodes for Wearable Biopotential Signal Monitoring: A Comprehensive Review. Biosensors vol. 13 Preprint at https://doi.org/10.3390/bios13070679 (2023).
Wei, B. et al., Ultraflexible tattoo electrodes for epidermal and in vivo electrophysiological recording. Cell Rep Phys Sci 4, (2023).
Ferrari, L. M., Ismailov, U., Badier, J. M., Greco, F. & Ismailova, E., Conducting polymer tattoo electrodes in clinical electro- and magneto-encephalography. npj Flexible Electronics 4, (2020).
Inzelberg, L., Rand, D., Steinberg, S., David-Pur, M. & Hanein, Y., A Wearable High-Resolution Facial Electromyography for Long Term Recordings in Freely Behaving Humans. Sci Rep 8, (2018).
Zhang, L. et al., Fully organic compliant dry electrodes self-adhesive to skin for long-term motion-robust epidermal biopotential monitoring. Nat Commun 11, (2020).
Hossain, M. M., Li, B. M., Sennik, B., Jur, J. S. & Bradford, P. D., Adhesive free, conformable and washable carbon nanotube fabric electrodes for biosensing. Flexible Electronics 6, (2022).
Takamatsu, S. et al., Direct patterning of organic conductors on knitted textiles for long-term electrocardiogra Sci Rep 5, (2015).
Nigusse, A. B., Mengistie, D. A., Malengier, B., Tseghai, G. B. & Van Langenhove, L., Wearable smart textiles for long-term electrocardiogramonitoring—a review. Sensors 21, (2021).
Charlton, P. H. et al., An impedance pneumography signal quality index: Design, assessment and application to respiratory rate monitoring. Biomed Signal Process Control 65, (2021).
Cebrián-Ponce, Áet al., Electrical Impedance Myography in Health and Physical Exercise: A Systematic Review and Future Perspectives. Frontiers in Physiology vol. 12 Preprint at https://doi.org/10.3389/fphys.2021.740877 (2021).
Rutkove, S. B., Electrical impedance myography: Background, current state, and future directions. Muscle and Nerve vol. 40 936-946 Preprint at https://doi.org/10.1002/mus.21362 (2009).
Stuart, T. et al., Biosymbiotic platform for chronic long-range monitoring of biosignals in limited resource settings. Proc Natl Acad Sci U S A 120, (2023).
Stuart, T. et al., Context-aware electromagnetic design for continuously wearable biosymbiotic devices. Biosens Bioelectron 228, (2023).
Stuart, T. et al., Biosymbiotic, Personalized, and Digitally Manufactured Wireless Devices for Indefinite Collection of High-Fidelity Biosignals. Sci. Adv vol. 7 https://www.science.org (2021).
Grimnes, S. & Martinsen, Ø. G., Passive Tissue Electrical Properties. in Bioimpedance and Bioelectricity Basics 77-118 (Elsevier, 2015). doi:10.1016/b978-0-12-411470-8.00004-0.
Stuart, T., Hanna, J., Gutruf, P., Wearable devices for continuous monitoring of biosignals: Challenges and opportunities, APL Bioengineering. 6, 021502 (2022).
Cai, Le et al., Osseosurface electronics—thin, wireless, battery-free and multimodal musculoskeletal biointerfaces, Nature Communications, 2021.
Ray, T. R. et al., Bio-integrated wearable systems: A comprehensive review. Chemical Reviews vol. 119 5461-5533 Preprint at https://doi.org/10.1021/acs.chemrev.8b00573 (2019).
Kim, D.-H. et al., Epidermal Electronics. https://www.science.org.
Zhang, Y. et al., Experimental and theoretical studies of serpentine microstructures bonded to prestrained elastomers for stretchable electronics. Adv Funct Mater 24, 2028-2037 (2014).
Rafeedi, T. et al., Wearable, epidermal devices for assessment of swallowing function. npj Flexible Electronics vol. 7 Preprint at https://doi.org/10.1038/s41528-023-00286-9 (2023).
Khang, D.-Y., Jiang, H., Huang, Y. & Rogers, J., A Stretchable Form of Single-Crystal Silicon for High-Performance Electronics on Rubber Substrates. Science (1979) 311, 208-212 (2006).
Matsunaga, Katsuji et al., Gas Permeability of Thermoplastic Polyurethane Elastomers, Polymer Journal, vol. 37, No. 7, pp. 413-417, 2005.

(56) References Cited

OTHER PUBLICATIONS

Koshi, T., Nomura, K., Yoshida, M., Measurement and analysis on failure lifetime of serpentine interconnects for e-textiles under cyclic large deformation, Flexible and Printed Electronics, 6 (2021) 025003, IOP Publishing Ltd.
Wang, S., Tang, S., He, C. & Wang, Q., Cyclic Deformation and Fatigue Failure Mechanisms of Thermoplastic Polyurethane in High Cycle Fatigue. Polymers (Basel) 15, (2023).
T. Stuart, et al., Biosymbiotic, personalized, and digitally manufactured wireless devices for indefinite collection of high-fidelity biosignals. Sci. Adv. 7, eabj3269 (2021).
N. Douthit, et al., Exposing some important barriers to health care access in the rural USA. Public Health 129, 611-620 (2015).
A. F. Cook, et al., Ethics and rural healthcare: What really happens? What might help? Am. J. Bioeth. 8, 52-56 (2008).
L. Kolobe, et al., Systematic literature survey: Applications of LoRa communications (2020).
N. Misran, et al., IoT based health monitoring system with LoRa communication technology in 2019 International Conference on Electrical Engineering and Informatics (ICEEI), (IEEE, 2019), pp. 514-517.
R. M. Sandoval, et al., Optimizing and updating lora communication parameters: A machine learning approach. IEEE Trans. Netw. Serv. Manag. 16, 884-895 (2019).
M. Cattani, et al., An experimental evaluation of the reliability of lora long-range low-power wireless communication. J. Sens. Actuator Networks 6, 7 (2017).
D. Yim, et al., An experimental LoRa performance evaluation in tree farm in 2018 IEEE Sensors Applications Symposium (SAS), (IEEE, 2018), pp. 1-6.
O. B. A. Seller, et al., Low power long range transmitter (2016).
J. Haxhibeqiri, et al., A survey of LoRaWAN for IoT: From technology to application. Sensors 18, 3995 (2018).
M. Bor, et al., LoRa transmission parameter selection in 2017 13th International Conference on Distributed Computing in Sensor Systems (DCOSS), (IEEE, 2017), pp. 27-34.
L. K. Ketshabetswe, et al., Communication protocols for wireless sensor networks: A survey and comparison. Heliyon 5, e01591 (2019).
S. Al-Sarawi, et al., Internet of Things (IoT) communication protocols in 2017 8th International Conference on Information Technology (ICIT), (IEEE, 2017), pp. 685-690.
A. Carlsson, et al., Measuring a LoRa network: Performance, possibilities and limitations in Internet of Things, Smart Spaces, and Next Generation Networks and Systems: 18th International Conference, NEW2AN 2018, and 11th Conference, RuSMART 2018, St. Petersburg, Russia, Aug. 27-29, 2018, Proceedings 18, (Springer, 2018), pp. 116-128.
J. M. Marais, et al., LoRa and LoRaWAN testbeds: A review. 2017 Ieee Africon, 1496-1501 (2017).
D. Bankov, et al., On the limits of LoRaWAN channel access in 2016 International Conference on Engineering and Telecommunication (EnT), (IEEE, 2016), pp. 10-14.
A. I. Petrariu, et al., Lorawan gateway: Design, implementation and testing in real environment in 2019 IEEE 25th International Symposium for Design and Technology in Electronic Packaging (SIITME), (IEEE, 2019), pp. 49-53.
S. Fahmida, et al., Long-lived LoRa: Prolonging the lifetime of a LoRa network in 2020 IEEE 28th International Conference on Network Protocols (ICNP), (IEEE, 2020), pp. 1-12.
Y. Li, et al., DyLoRa: Towards energy efficient dynamic LoRa transmission control in IEEE Infocom 2020—IEEE Conference on Computer Communications, (IEEE, 2020), pp. 2312-2320.
Y. Yazid, et al., On the LoRa performances under different physical layer parameter selection in 2020 International Symposium on Advanced Electrical and Communication Technologies (ISAECT), (IEEE, 2020), pp. 1-6.
F. Cuomo, et al., EXPLoRa: Extending the performance of LoRa by suitable spreading factor allocations in 2017 IEEE 13th International Conference on Wireless and Mobile Computing, Networking and Communications (WiMob), (IEEE, 2017), pp. 1-8.
H. M. Madjar, Human radio frequency exposure limits: An update of reference levels in Europe, USA, Canada, China, Japan and Korea in 2016 International Symposium on Electromagnetic Compatibility—EMC Europe, (IEEE, 2016), pp. 467-473.
J. A. C. Patterson, et al., A flexible, low noise reflective PPG sensor platform for ear-worn heart rate monitoring in 2009 Sixth International Workshop on Wearable and Implantable Body Sensor Networks, (IEEE, 2009), pp. 286-291.
J. Kim, et al., Miniaturized Battery-Free Wireless Systems for Wearable Pulse Oximetry. Adv. Funct. Mater. 27, 1604373 (2017).
A. A. Alian, et al., Photoplethysmography. Best Pract. Res. Clin. Anaesthesiol. 28, 395-406 (2014).
J. Allen, Photoplethysmography and its application in clinical physiological measurement. Physiol. Meas. 28, R1 (2007).
J. Yang, et al., Beyond beaconing: Emerging applications and challenges of BLE. Ad hoc networks 97, 102015 (2020).
F. J. Dian, et al., A practical study on Bluetooth Low Energy (BLE) throughput in 2018 IEEE 9th Annual Information Technology, Electronics and Mobile Communication Conference (IEMCON), (IEEE, 2018), pp. 768-771.
L. Schauer, et al., Potentials and limitations of wifi-positioning using time-of-flight in International Conference on Indoor Positioning and Indoor Navigation, (IEEE, 2013), pp. 1-9.
J. Simo, et al., Distance limits in IEEE 802.11 for rural networks in developing countries. IEEE WRECOM (2007).
International Search Report and Written Opinion of International Application No. PCT/US23/36795, mail date Apr. 11, 2024, 14 pages.
International Preliminary Report on Patentability of International Application No. PCT/US2023-036795, issued Apr. 29, 2025, 9 pages.
Heikenfeld, J. et al. Wearable sensors: modalities, challenges, and prospects. Lab Chip 18, 217-248 (2018).
Cho, S., Ensari, I., Weng, C., Kahn, M. G. & Natarajan, K. Factors affecting the quality of person-generated wearable device data and associated challenges: Rapid systematic review. JMIR Mhealth Uhealth 9, e20738 (2021).
Mercer, K. et al. Acceptance of Commercially Available Wearable Activity Trackers Among Adults Aged Over 50 and With Chronic Illness: A Mixed-Methods Evaluation. JMIR Mhealth Uhealth 4, e7 (2016).
Kekade, S. et al. The usefulness and actual use of weearable devices among the elderly population. Comput Methods Programs Biomed 153, 137-159 (2018).
Fensli, R., Pedersen, P. E., Gundersen, T. & Hejlesen, O. Sensor acceptance model-measuring patient acceptance of wearable sensors. Methods Inf Med 47, 89-95 (2008).
Spagnolli, A., Guardigli, E., Orso, V., Varotto, A. & Gamberini, L. Measuring user acceptance of wearable symbiotic devices: validation study across application scenarios. in International Workshop on Symbiotic Interaction 87-98 (Springer, 2015).
Yin, Z., Yan, J., Fang, S., Wang, D. & Han, D. User acceptance of wearable intelligent medical devices through a modified unified theory of acceptance and use of technology. Ann Transl Med 10, (2022).
Lim, H. et al. Advanced soft materials, sensor integrations, and applications of wearable flexible hybrid electronics in healthcare, energy, and environment. Advanced Materials 32, 1901924 (2020).
Ray, T. et al. Soft, skin-interfaced wearable systems for sports science and analytics. Curr Opin Biomed Eng 9, 47-56 (2019).
Sunwoo, S.-H., Ha, K.-H., Lee, S., Lu, N. & Kim, D.-H. Wearable and implantable soft bioelectronics: Device designs and material strategies. Annu Rev Chem Biomol Eng 12, 359-391 (2021).
A, R. J., Takao, S. & Yonggang, H. Materials and Mechanics for Stretchable Electronics. Science (1979) 327, 1603-1607 (2010).
Dang, Q. H., Chen, S. J., Ranasinghe, D. C. & Fumeaux, C. Modular Integration of a Passive RFID Sensor With Wearable Textile Antennas for Patient Monitoring. IEEE Trans Compon Packaging Manuf Technol 10, 1979-1988 (2020).
Shadid, R. & Noghanian, S. A literature survey on wireless power transfer for biomedical devices. Int J Antennas Propag 2018, (2018).

(56) References Cited

OTHER PUBLICATIONS

Zou, Y., Bo, L. & Li, Z. Recent progress in human body energy harvesting for smart bioelectronic system. Fundamental Research 1, 364-382 (2021).
Xu, C., Song, Y., Han, M. & Zhang, H. Portable and wearable self-powered systems based on emerging energy harvesting technology. Microsyst Nanoeng 7, 1-14 (2021).
Choi, Y.-M., Lee, M. G. & Jeon, Y. Wearable biomechanical energy harvesting technologies. Energies (Basel) 10, 1483 (2017).
Nozariasbmarz, A. et al. Review of wearable thermoelectric energy harvesting: From body temperature to electronic systems. Appl Energy 258, 114069 (2020).
Tucker, S. et al. Biosymbiotic, personalized, and digitally manufactured wireless devices for indefinite collection of high-fidelity biosignals. Sci Adv 7, eabj3269 (2021).
International Search Report and Written Opinion from related PCT/US2021/012918 mailed Mar. 25, 2021.
Majumder et al., "Wearable Sensors for Remote Health Monitoring", McMaster University, Jan. 12, 2017.
Song et al., "Stretchable antenna for wearable health monitoring", North Carolina State University, Mar. 18, 2014.
Manjakkal, et al., "Flexible self-charging supercapacitor based on graphene-Ag-3D graphene foam electrodes", University of Glasgow, Mar. 10, 2018.
"Global Wearable Medical Devices Market 2018-2022." PRNewswire.com. PR Newswire, Feb. 5, 2018. Web. Feb. 18, 2019. https://www.prnewswire.com/news-releases/global-wearable-medical-devices-market-2018-2022-by-device-diagnostic-therapeutic-application-sport-fitness-rpm-type-smartwatch-patch-distribution-channel-pharmacy-online-300593282.html.
Ajami, Sima. "Wearable Biosensors for Monitoring Patients." ResearchGate.net. ResearchGate, May 2016. Web. Feb. 20, 2019. https://www.researchgate.net/publication/303368284_Wearable_biosensors_for_monitoring_patients.
International Preliminary Report on Patentability from corresponding PCT Appln. No. PCT/us2021/01918, dated Jul. 12, 2022. 8 pages.
NonFinal Office Action of U.S. Appl. No. 17/791,523, mail date Nov. 29, 2024, 11 pages.
Final Office Action of U.S. Appl. No. 17/791,523, mail date May 21, 2025, 11 pages.
NonFinal Office Action of U.S. Appl. No. 17/791,523, mail date Oct. 1, 2025, 14 pages.

* cited by examiner 148
150
188a
166
170a
162
160a
184
149, 188
149, 192
163

THREE-DIMENSIONAL PRINTED ARTICLES AND METHODS OF MANUFACTURE

CROSS REFERENCE TO RELATED APPLICATIONS

This application is a U.S. National Stage filing of PCT/US22/20030, filed Mar. 11, 2022, and claims the benefit of U.S. Provisional Application No. 63/159,884, filed Mar. 11, 2021, both of which are hereby incorporated by reference in their entirety.

SUMMARY

Three-dimensionally (3D) printed, wearable, electronic sensing articles and methods of manufacture are disclosed. A 3D digital (computer) model of a body of a particular (unique) wearer may be obtained by 3D mapping, such as CT scan, MRI scan, photogrammetric mapping and/or 3D scanning, etc. Data from a 3D dataset of the 3D digital mathematical representation of the wearer's body may then be manipulated via software to create a two-dimensional (2D) template, particularly by unfolding the 3D dataset. The two-dimensional (2D) template may then be used to generate the 3D printed personalized wearable electronic article, which may comprise a mesh as a base structure, which is custom (uniquely) fitted to the wearer's body. The mesh may be formed of an elastomeric polymer composition, to provide a mesh which is flexible, soft and stretchable (elastic), whereby the mesh is conformable (e.g. circumferentially) to changes in body shape of the wearer's body during movement, particularly by elastic deformation. This individually tailored fit may provide an at least substantially perfect conformality to the wearer's body, enabling high-fidelity and chronic biodata acquisition that is adhesive-free (i.e. no adhesive is required to bond the sensing article to the body of the wearer). It may be understood that wearables that require use of an adhesive to be attached to the wearer's body generally may only be used for periods of continuous attachment which is less than one week, and which are at best limited to two weeks. However, given the wearable articles of the present disclosure do not require use of an adhesive to be attached to the wearer's body, the wearable articles of the present disclosure are not so limited and may be continuously attached to the wearer's body for periods which may exceed two weeks. Moreover, the wearable articles of the present disclosure may be removed from the body and subsequently reapplied, whereas wearables that require use of an adhesive to be attached to the wearer's body are generally single use.

BACKGROUND

Current sensing technologies have recently advanced significantly with the introduction of epidermal electronics, epifluidics and wireless, battery-free electronics that enable recording and capture of clinical-grade biophysical data from subjects without need of cumbersome conventional tools that inhibit the wearer's mobility with a need for constant user or patient interaction. A common issue in the creation of these types of physiological, as well as biofluid, sensors systems is the complex development process and subsequently long development time that make it nearly impossible to create custom-made devices specifically tailored towards specific biomarkers or use cases. The advantage of a custom-made sensor system, however, would ensure the highest sensing fidelity through intimate skin contact in a form factor that does not require skin adhesives and reduces bulk to the point of imperceptible feel. Additional challenges include the user interaction that is required with current wearable systems, which either require the need to recharge batteries or wired hardware in close proximity of data collection devices, limiting experimental, clinical and commercial paradigms, inhibiting functional use cases significantly.

BRIEF DESCRIPTION OF THE DRAWINGS

Features and advantages of this disclosure will become more apparent as the following detailed description proceeds, and upon reference to the drawings, wherein like numerals designate like parts, and in which.

DETAILED DESCRIPTION

Figure 1:
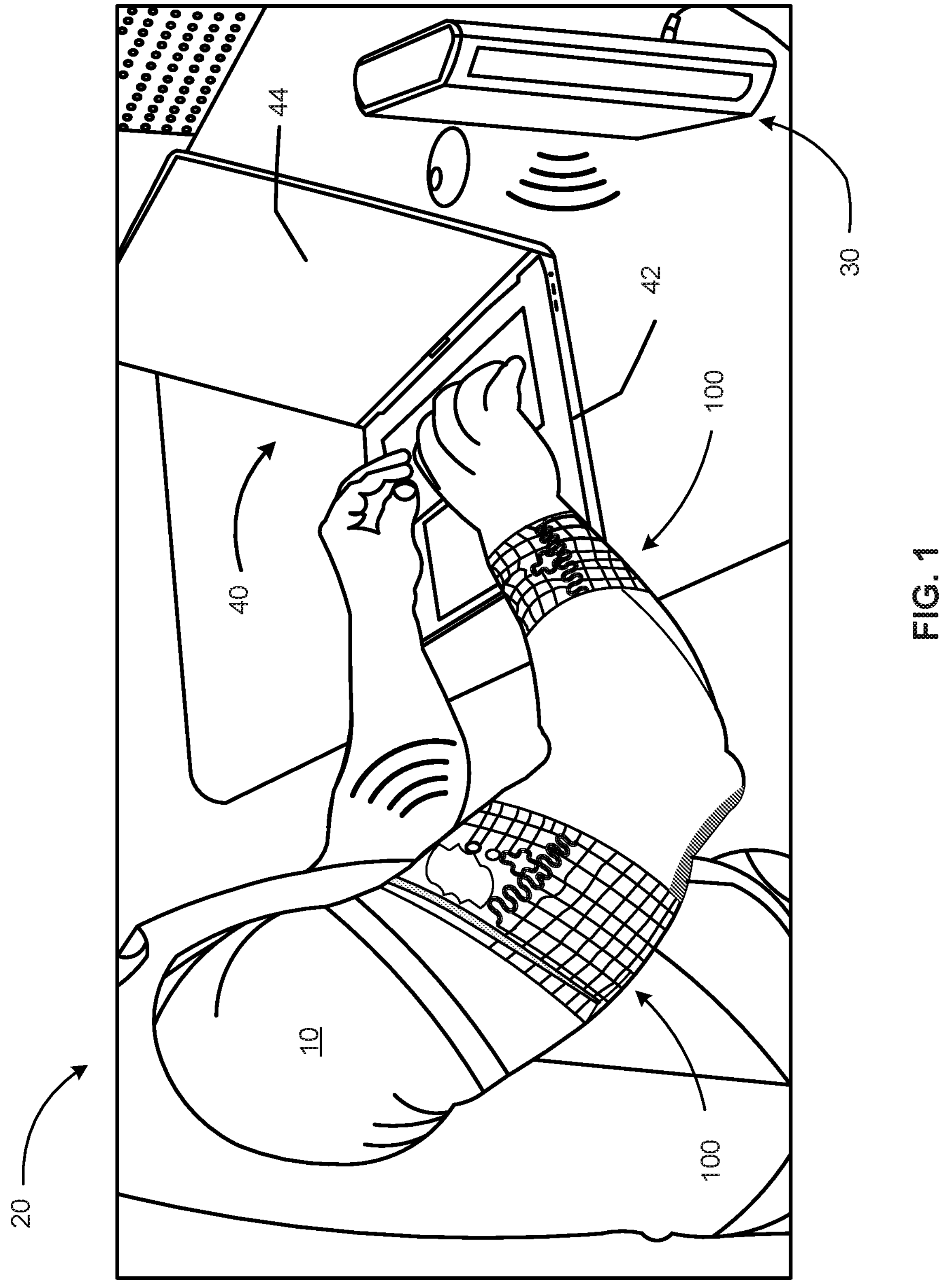
FIG. 1 is a view of a system according to the present disclosure, particularly a healthcare monitoring and/or diagnostic system, which comprises a three-dimensionally (3D) printed sensing article.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Throughout the description, like reference numerals and letters indicate corresponding structure throughout the drawings/embodiments and, as such, corresponding structure may not be separately discussed as merely being repetitive. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive.

To address the foregoing challenges, the present disclosure provides three-dimensionally printed, wearable, electronic, sensing articles, particularly which may further be wireless, battery-free, non-invasive and personalized to the body of the wearer and entirely digitally manufactured. The sensing article may particularly comprise an elastomeric base (backbone/platform) structure, comprising a mesh, formed of one or more 3D printed elastomeric polymer compositions to provide a base/mesh which is flexible, soft and stretchable (elastic), whereby the base/mesh is conformable (e.g. circumferentially) to changes in body shape of the wearer's body during movement, particularly by elastic deformation. 3D printing enables digital control over geometry, allowing for tailored designs, topologies, and sensor locations that are specific to diagnosis and patient needs. The elastomeric base/mesh provides favorable mechanical properties similar to the epidermis, enabling intimate contact of sensor nodes to the body and increasing signal fidelity due to lowered skin impedance (thermal, electrical, and mechanical). Embedded/encapsulated in the elastomeric base/mesh is a soft antenna structure that incorporates a far-field energy harvesting system that operates at 915 MHz, a widely used frequency for wireless power transfer systems approved by the United States Federal Communications Commission.

While portions of the sensing articles described herein are described as being three-dimensionally printed, such should be understood as being preferred, particularly when the article is personalized to the body of the wearer, i.e. formed with photogrammetric mapping. However, it should be appreciated that the articles do not necessarily need to be personalized to the body of the wearer or three-dimensionally printed. For example, the portions of the sensing articles described herein as being three-dimensionally printed may be injection molded using thermoplastic elastomer, or laser cut from thermoplastic elastomer sheet (e.g. to form the mesh herein). Moreover, the articles may be produced in different sizes (e.g. small, medium and large) to fit bodies of different size.

Referring to FIG. 1, there is shown a system 20, and particularly a healthcare monitoring and/or diagnostic system, according to the present disclosure. As shown, the system 20 comprises a wireless power caster/transmitter device 30, a sensing (biosymbiotic) article 100 (disposed on a human (host) body 10) and a remote wireless electronic (data collection) device 40. As shown, the remote electronic (data collection) device 40 may be a computer 42 such as a desktop computer, a portable computer such as a laptop computer, a notebook computer, a netbook (with or without a keyboard such as an iPad), a personal digital assistant (PDA), a cellphone computer or other handheld computer (e.g. smartphone). Computer 42 includes a visual display 44, which may be understood as a computer output surface and projecting mechanism that shows text and often graphic images (e.g. as part of a graphical user interface) to the computer user (which may be the host of the sensing article 100), such as via a liquid crystal display (LCD), light-emitting diode (LED), gas plasma (GS), or other image projection technology. The display 44 may be a touch activated display.

The sensing articles 100 disclosed herein are three-dimensionally (3D) printed, wearable, electronic, sensing articles 100, particularly to be worn directly on the epidermis (and hence may also be considered epidermal). The sensing articles 100 may also be wireless, battery-free, non-invasive and personalized to the body 10 of the wearer.

Figure 2:
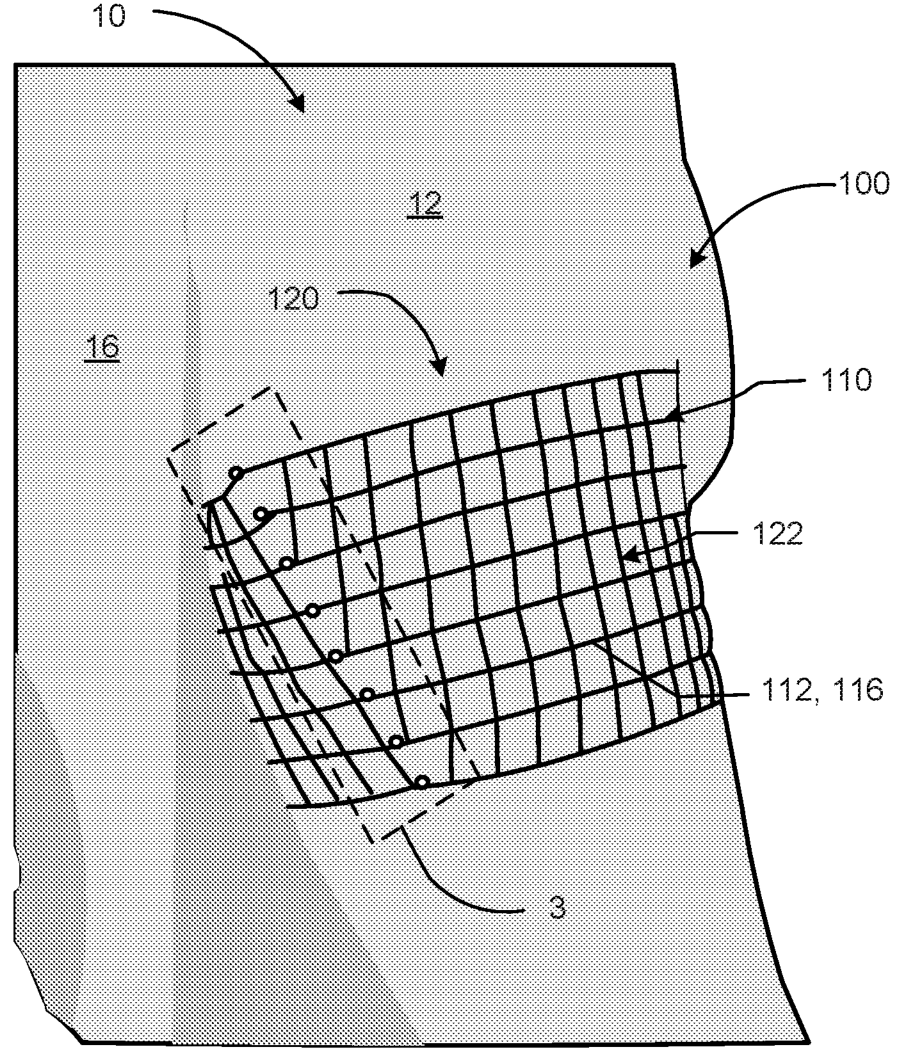
FIG. 2 is a view of a three-dimensionally printed sensing article disposed on a human body.

As discussed in greater detail, infra, a sensing article 100 is three-dimensionally (3D) printed in a two-dimensional (planar) form, and may be subsequently wrapped circumferentially around the body 10, particularly fully around (i.e. 360 degrees) an appendage 12 of the body 10 such as an arm or leg, or the torso 16. As shown in FIG. 2, the sensing device 100 is wrapped around the upper arm, particularly around the area of the bicep and tricep.

Figure 3:
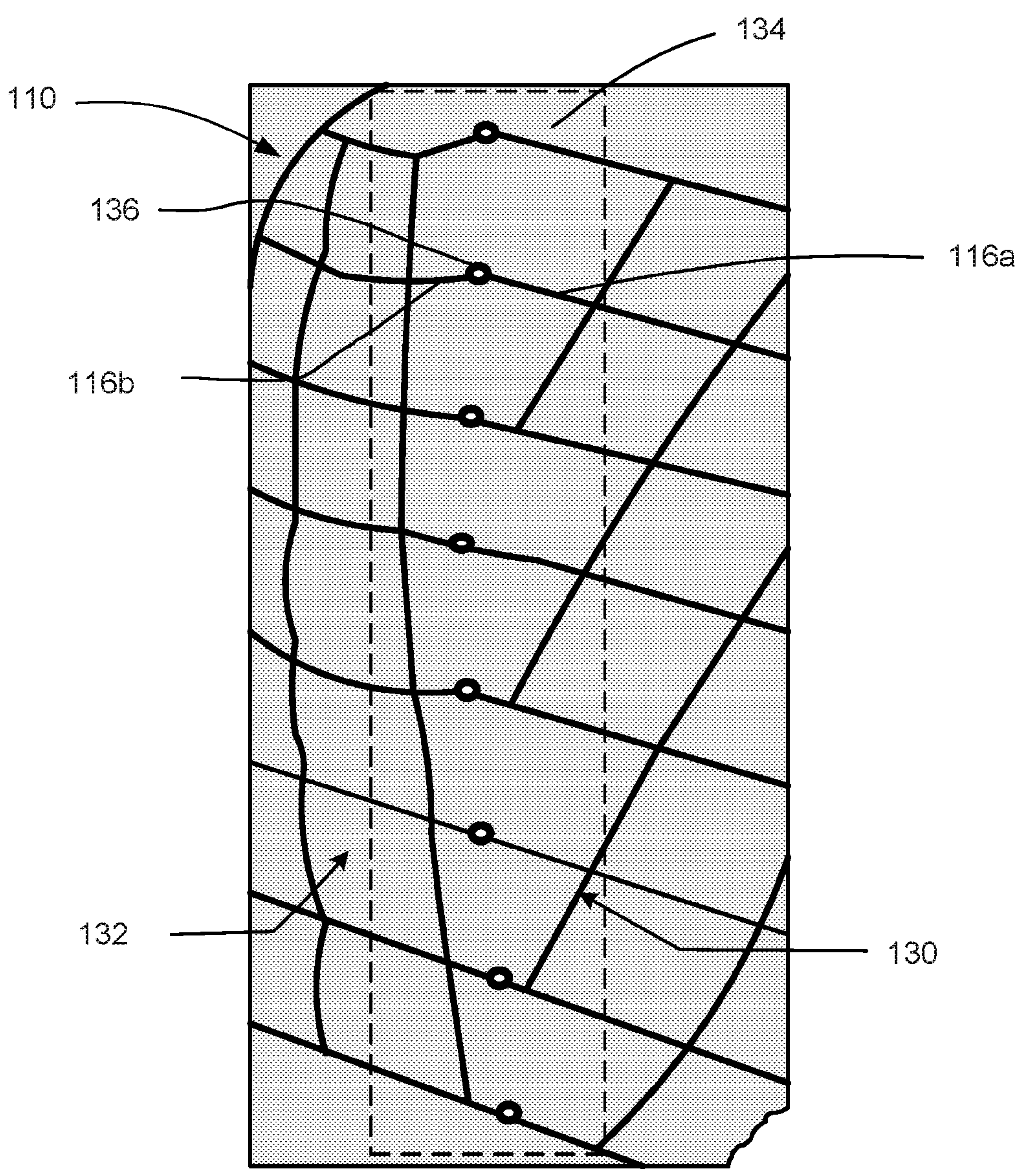
FIG. 3 is a close-up view of the region of FIG. 2 bounded by rectangle 3.
Figure 4:
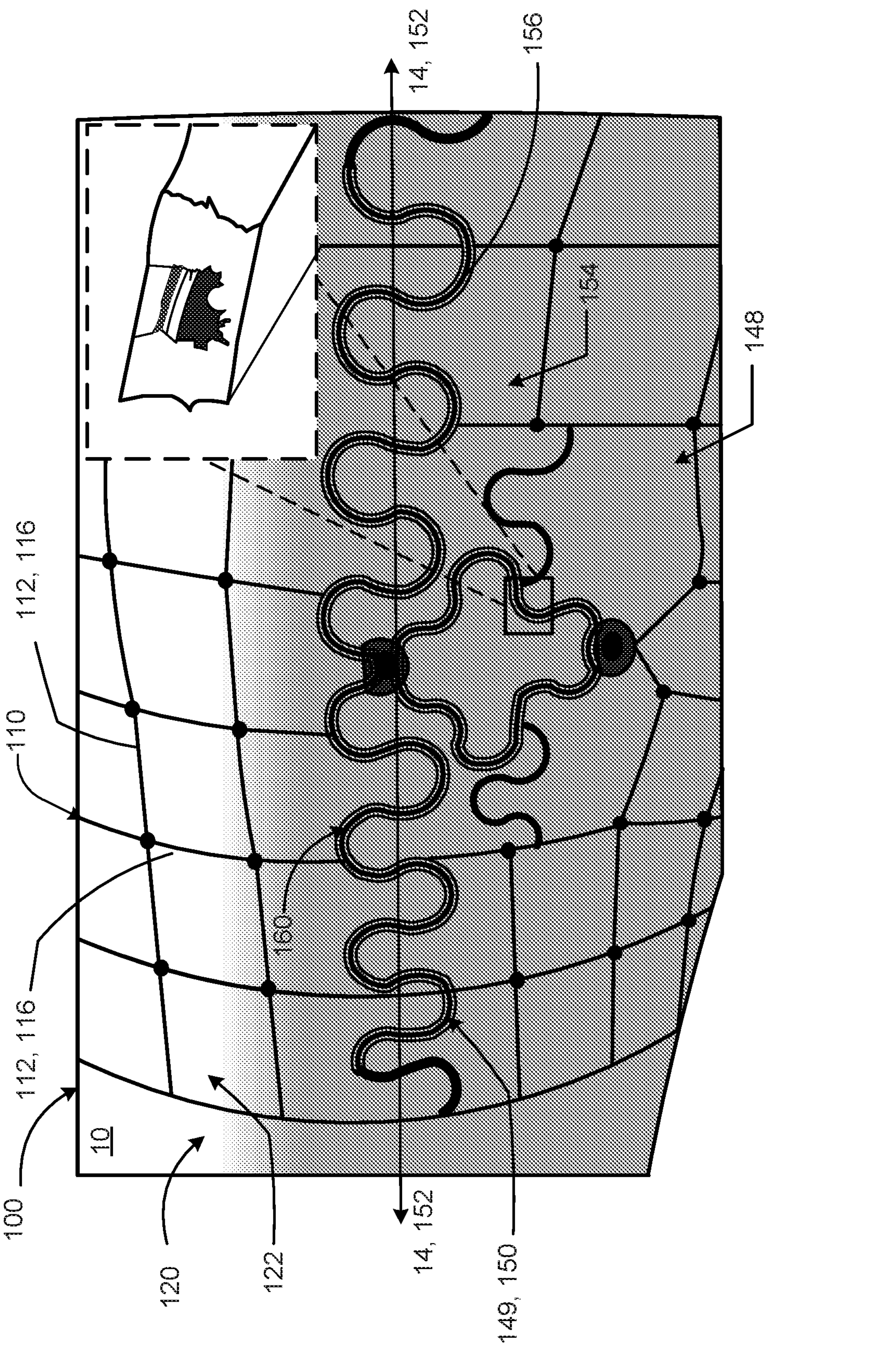
FIG. 4 is a view of a three-dimensionally printed sensing article disposed on a human body, including an electronic structure, particularly an antenna structure for power receiving (harvesting) from an external wireless power source, and a close up cross-sectional view of electronic components of the electronic structure embedded/encapsulated in a three-dimensionally printed electronic enclosure of the electronic structure.

As shown in FIGS. 2-4, the sensing article 100 comprises a 3D printed elastomeric platform base 110, particularly in a form of a mesh 112 comprising a plurality of intersecting (e.g. transverse) strut segments 116 arranged in a lattice structure 120, particularly in which at least some of the strut segments 116 are arranged substantially parallel or perpendicular (e.g. in a range of 0.1 degrees to 10 degrees of being parallel or perpendicular, and more particularly in a range of 0.1 degrees to 5 degrees of being parallel or perpendicular) to one another as to create a grid of polygonal (quadrilateral and more particularly a rectangular or square) shaped window openings 122.

The individual strut segments 116 may have a cross-sectional shape which may be polygonal (e.g. quadrilateral and more particularly rectangular or square). The cross-sectional area of the individual strut segments 116 may be in a range of 0.06 $mm^2$ to 1 $mm^2$, and more particularly in a range of 0.16 $mm^2$ to 0.64 $mm^2$. The window openings 122 may have an area in a range of 16 $mm^2$ to 225 $mm^2$, and more particularly in a range of 36 $mm^2$ to 144 $mm^2$. The base 110/mesh 112/struts 116 may be made of thermoplastic elastomer, particularly thermoplastic polyurethane.

As shown in FIGS. 2-3, opposing end regions 130, 132 of the base 110/mesh 112 may be joined at a seam 134. As shown, the seam 134 is formed by cantilevered strut segments 116*a* of end region 130 which are connected in one-to-one relationship to cantilevered strut segments 116*b* of end region 132. The pairs of connected strut segments 116*a*, 116*b* may be joined by first placing the unconnected pairs of strut segments 116*a*, 116*b* side-by side such that at least a portion of their longitudinal lengths overlap. Thereafter, the overlapping portions may be heated, melted, pressed together and subsequently cooled (e.g. melt bonded) to join the pairs of strut segments 116*a*, 116*b* and end regions 130, 132 together at head/joint 136. In the foregoing manner, the end regions 130, 132 of the base 110/mesh 112 are mechanically integrally connected monolithically (i.e. from the material of the one-piece base 110/mesh 112 without need for separate fasteners). However, it should be understood that connection of the end regions 130, 132 is not limited to the foregoing, and the end regions 130, 132 may be connected with any suitable permanent (non-releasable) or releasable fasteners (e.g. heat shrink tubing, butt connectors, splice connectors, hook and loop connectors).

Now referring to FIGS. 4-6B, the article 100 may further comprise an electronic structure 148 which comprises an electronic component 149 in a form of an antenna 150, and more particularly a wireless energy harvesting antenna 150, which also may be referred to as a rectenna or rectifying antenna, which operates as part of a far-field (radio frequency), wireless, energy harvesting/power management device 102 (see FIGS. 8-9) of article 100. As explained in greater detail, infra, the antenna 150 harvests energy from the power caster device 30, particularly to power electronic components 149 of the sensing article 100 which consume power (e.g. data collection sensors 196).

As shown, the antenna 150 comprises an antenna structure having a curvilinear (serpentine/oscillating) repeating wave shape 154 which may extend in an antenna longitudinal direction 152, which, as shown, is also a transverse direction relative to the sensing article longitudinal direction 158. When sensing article 100 is disposed on the body 10 (e.g. extending/wrapped around an appendage 12), the antenna longitudinal direction 152 extends along the longitudinal (proximal-distal) direction 14 of the appendage 12, while the sensing article longitudinal direction 158 extends in a circumferential direction around the appendage 12. As shown, the wave shape 154 is formed by a plurality of alternating, reverse semi-circular (e.g. in a range of 180-200 degrees) segments 156 arranged adjacent one another end to end in the antenna longitudinal direction 152.

Figure 5:
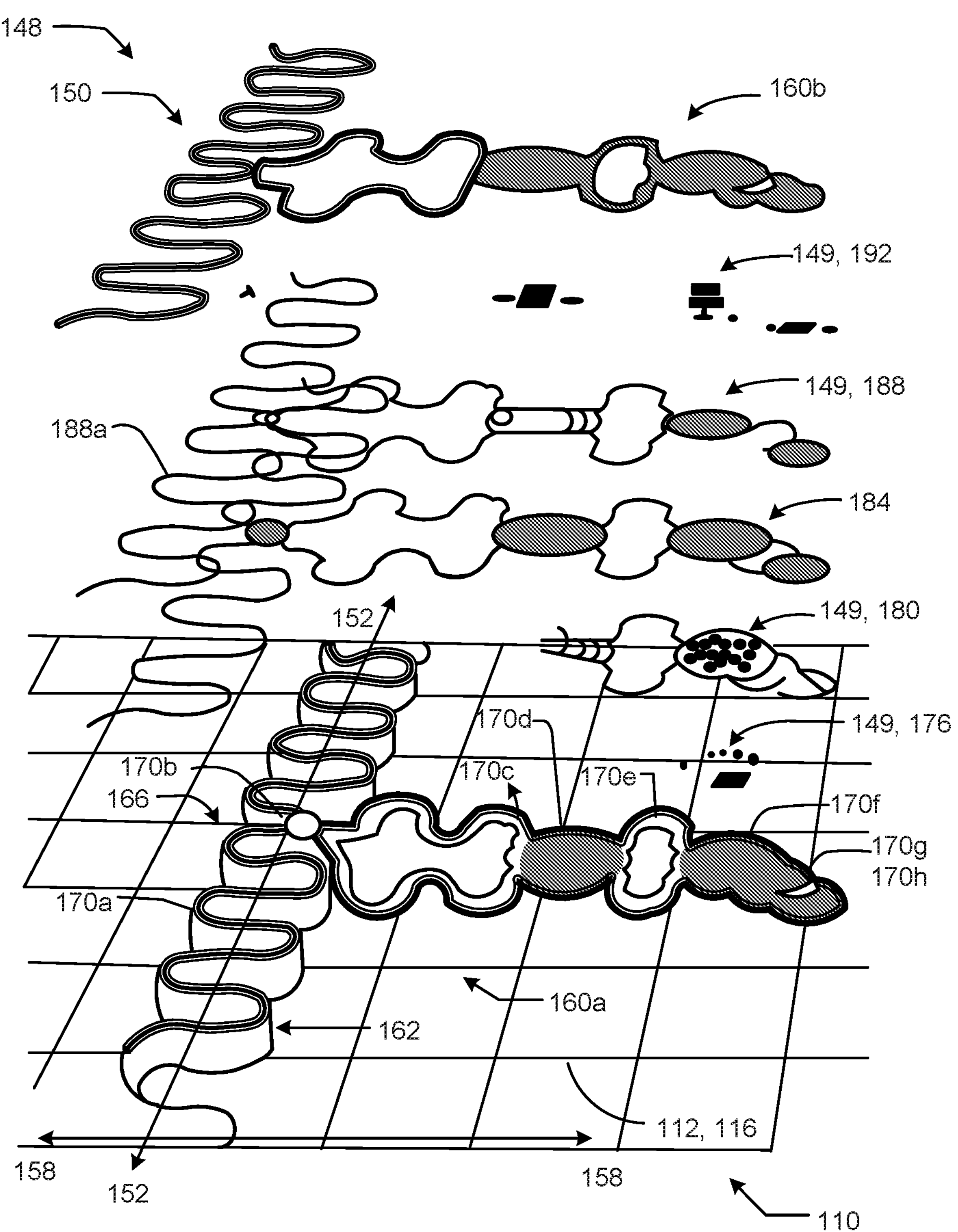
FIG. 5 is a close-up exploded view of an electronic structure of a three-dimensionally printed sensing article.

The antenna electronic components, along with other electronic components 149 discussed in further detail, infra, are at least partially embedded/encapsulated, and more particularly preferably fully embedded/encapsulated, within a three-dimensionally 3D printed electronic component enclosure 160 of the sensing article 100, which is shown in FIG. 5 as a lower enclosure 160*a* and an upper enclosure 160*b* for purposes of illustration.

The electronic enclosure 160 may be formed of the same three-dimensionally (3D) printed elastomeric material as the base 110/mesh 112 and thus formed as one-piece with the base 110/mesh 112. The enclosure 160 may be in the same plane as the strut segments 116 of the base 110/mesh 112, in which case the strut segments 116 are connected laterally to a vertical side 162 of the enclosure 160, and to not extend underneath the enclosure 160. Alternatively, as shown in FIG. 6C, the enclosure 160 may be disposed on top of (i.e. raised above/overlie) the strut segments 116 of the base 110/mesh 112, in which case the strut segments 116 are connected to a bottom side 164 of the enclosure 160. Moreover, it should be understood that, in certain embodiment, certain strut segments 116 may be connected laterally to the vertical side 162 of the enclosure 160, while other strut segments 116 may be connected to the bottom side 164 of the enclosure 160.

During manufacture, the top side 166 of the lower enclosure 160*a* may be formed with a recess 170, which may be further divided into connected recesses 170*a*, 170*b*, 170*c*, 170*d*, 170*e*, 170*f*, 170*g*, 170*h*, to arrange and immobilize the various electronic components 149 of the sensing article 100 while the upper enclosure 160*b* is formed in situ on the lower enclosure 160*a*. As shown, recesses 170*a*, 170*c*, 170*e* and 170*g* are elongated grooves, while recesses 170*b*, 170*d*, 170*f* and 170*h* are circular nodes.

Once the lower enclosure 160*a* is formed with recess 170, a layered electronic structure may then be disposed in the recess 170. The layered structure, may comprise in ascending order lower electronic components 176, lower electrical power (flexible metal copper) conductor 180, electrical (flexible plastic polyimide) insulator 184, upper electrical power (flexible metal copper) conductor 188 and upper electronic components 192. Apart from the antenna electronic components, the electronic components 149, including components 176, 192, as discussed in further detail, infra, may include data collection sensors such as temperature sensors, accelerometers, epifluidic (sweat) sensors and strain gauge sensors; an AC to DC rectifier; a power management integrated circuit (IC); an energy storage device, such as a super capacitor and/or a battery; and a System on a Chip (SoC) with wireless (Bluetooth) communication. Thus, the electronic enclosure 160 may further comprise, for example, an antenna enclosure, a temperature sensor enclosure, an accelerometer enclosure and epifluidic sensor enclosure and a strain gauge enclosure, an AC to DC rectifier enclosure; a power management integrated circuit (IC) enclosure; an energy storage device enclosure, such as a super capacitor and/or a battery enclosure, and a System on a Chip enclosure. It should be understood that all the foregoing structures are not necessarily required. For example, as shown in FIG. 6, in certain embodiments the lower electronic components 176 and lower electrical power (flexible metal copper) conductor 180 may be eliminated.

Once the foregoing structures are disposed in recess 170, the upper enclosure 160*b* is formed in situ on the lower enclosure 160*a*, whereby the contents of the sensing article 100 disposed in the recess 170 are now fully embedded/encapsulated in a closed cavity (see inset of FIG. 4).

Figures 6, 6A, 6B:
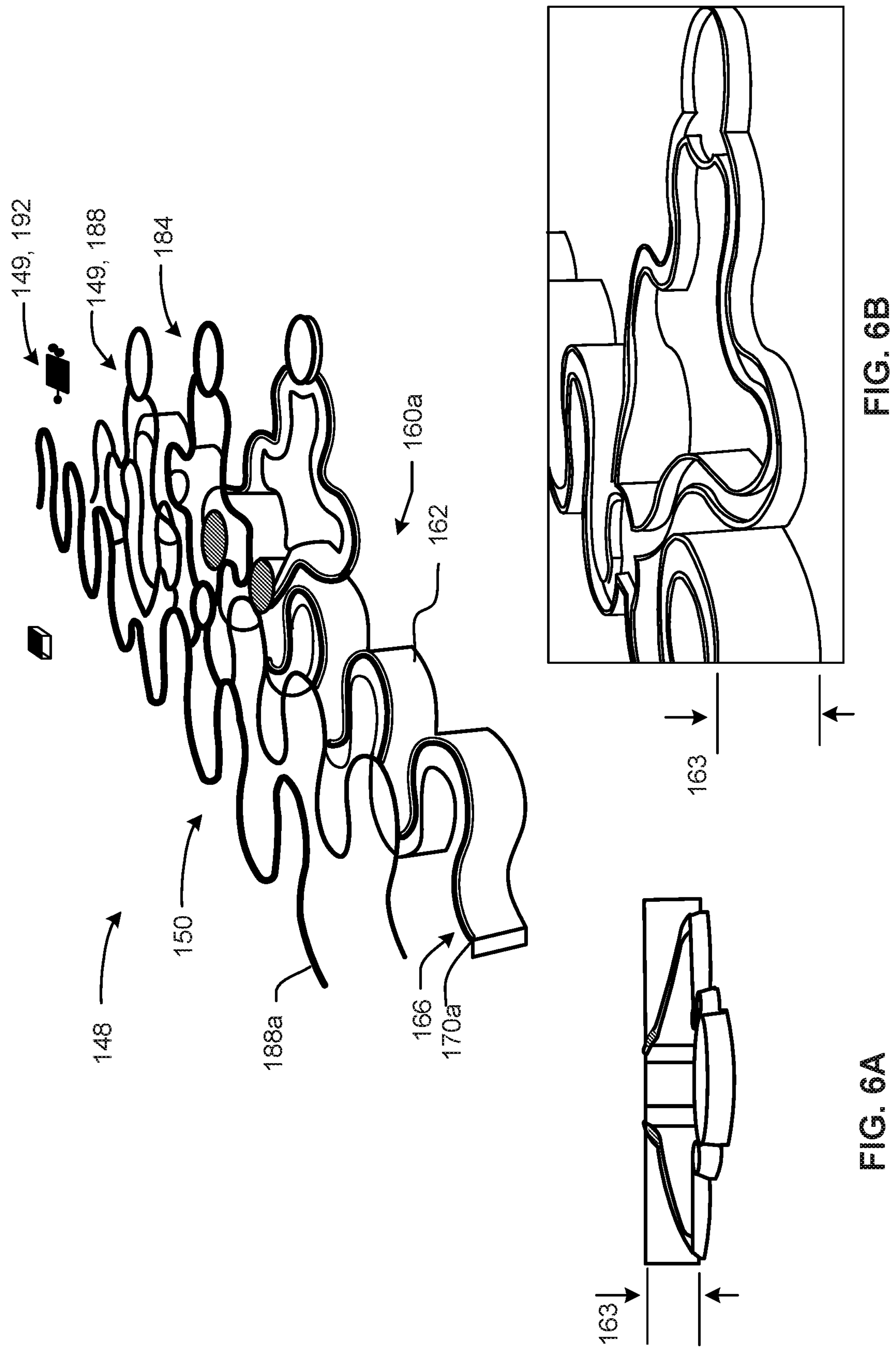
FIG. 6 is a close-up exploded view of an electronic structure of a three-dimensionally printed sensing article.
FIG. 6A is a close-up side view of a lower portion of an electronic enclosure of the electronic structure of FIG. 6.
FIG. 6B is a close-up perspective view of the lower portion of the electronic enclosure of the electronic structure of FIG. 6.
Figure 6C:
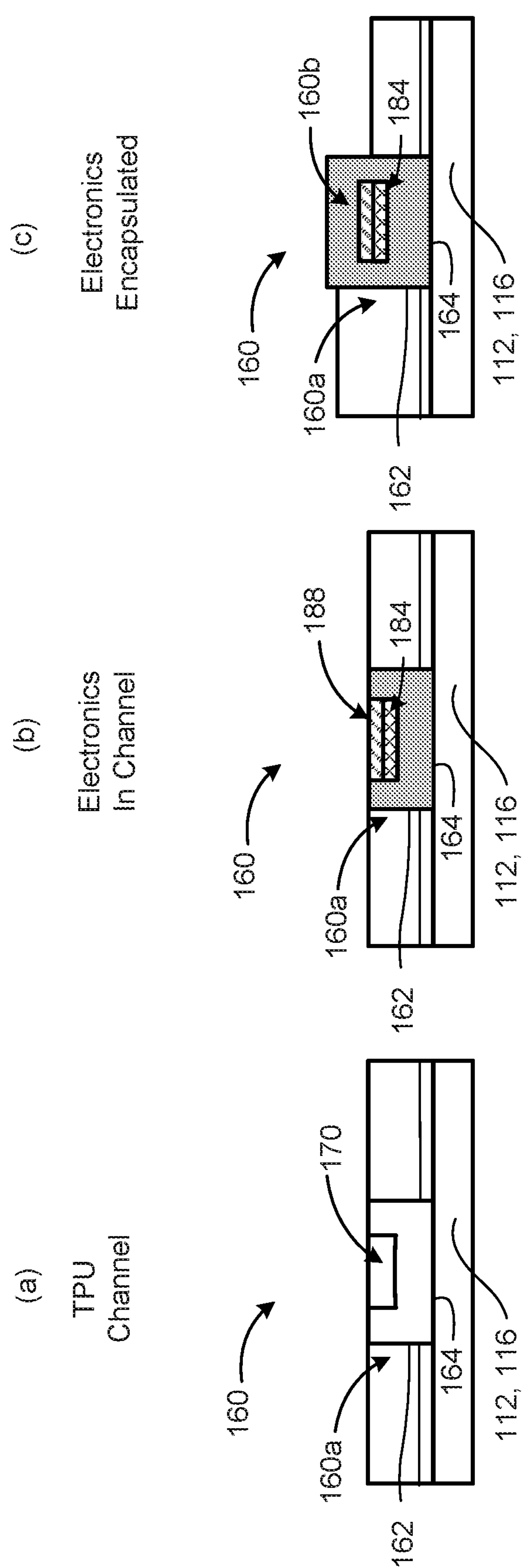
FIG. 6C are cross-sectional views of electronic component encapsulation in the electronic enclosure during fabrication of the three-dimensionally printed sensing article.

As best shown by FIGS. 6A-6B, certain electronic components 149 may be vertically raised in the enclosure 160 relative to other electronic components 149, such that the electronic components 149 are further away from the body 10 when the sensing article 100 is disposed thereon. More particularly, the antenna (power receptor) segment 188*a* of the electrical power conductor 188 is vertically raised away from the body 10, particularly by a vertical height 163 of the lower enclosure 160*a*. The antenna (power receptor) segment 188*a* is raised away from the body 10 to reduce electromagnetic interference from the body 10 from inhibiting power transmission to the antenna 150.

In FIG. 6C, the lower structure 160*a* disposed on top of (i.e. raised above/overlie) the strut segments 116 of the base 110/mesh 112, in which case the strut segments 116 are connected to a bottom side 164 of the lower enclosure 160*a*.

Figure 7:
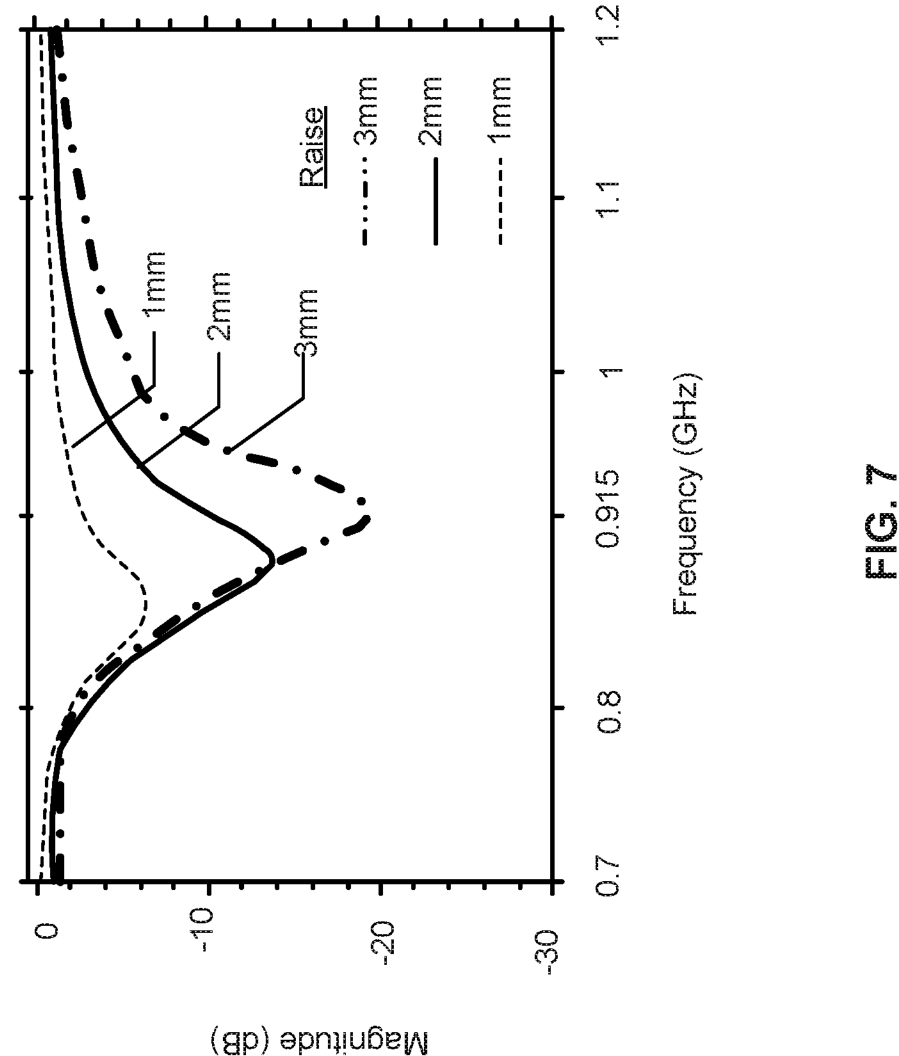
FIG. 7 is a graph of magnitude (decibels) as a function of frequency (gigahertz) of the antenna structure for varying distance/height (millimeters) of the antenna structure (e.g. from the body)

FIG. 7 shows a measurement of the performance of the antenna 150 of the sensing article 100 on the body 10, particularly a wrist. More particularly, FIG. 7 shows simulation results when the antenna (power receptor) segment 188*a* of the antenna 150 is raised to different heights 163 (i.e. raised levels) in a range of 1 mm to 3 mm from the body 10. 3D printing of topologically complex structures of the sensing article 100 enables the implementation and improved performance of the antenna 150.

Figure 8:
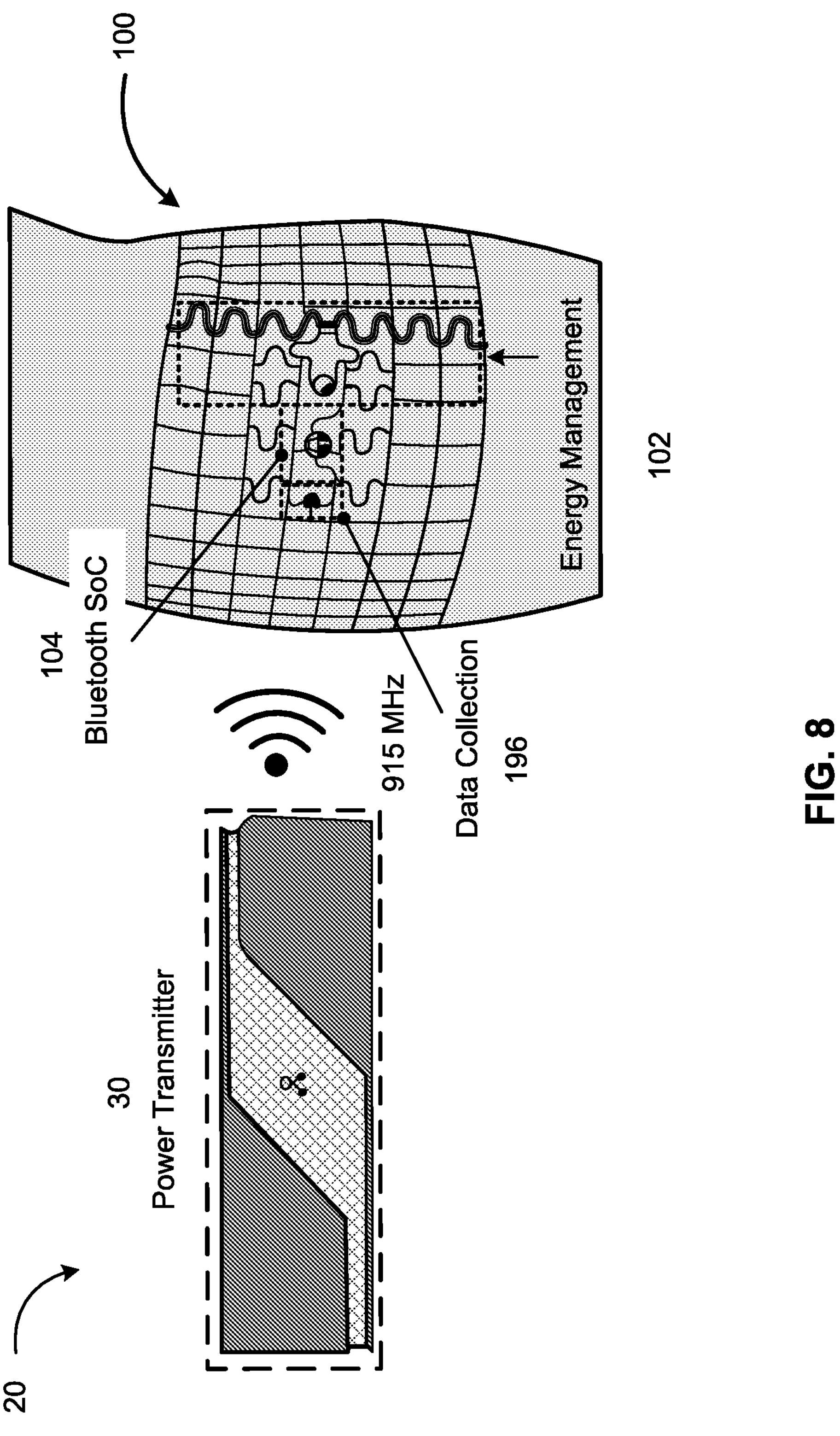
FIG. 8 a view of a system according to the present disclosure, particularly a healthcare monitoring and/or diagnostic system, which comprises a three-dimensionally printed sensing article comprising electronic components, such as wireless power receiving (harvesting) components, wireless communication components and electronic data collection (sensing) components.
Figure 9:
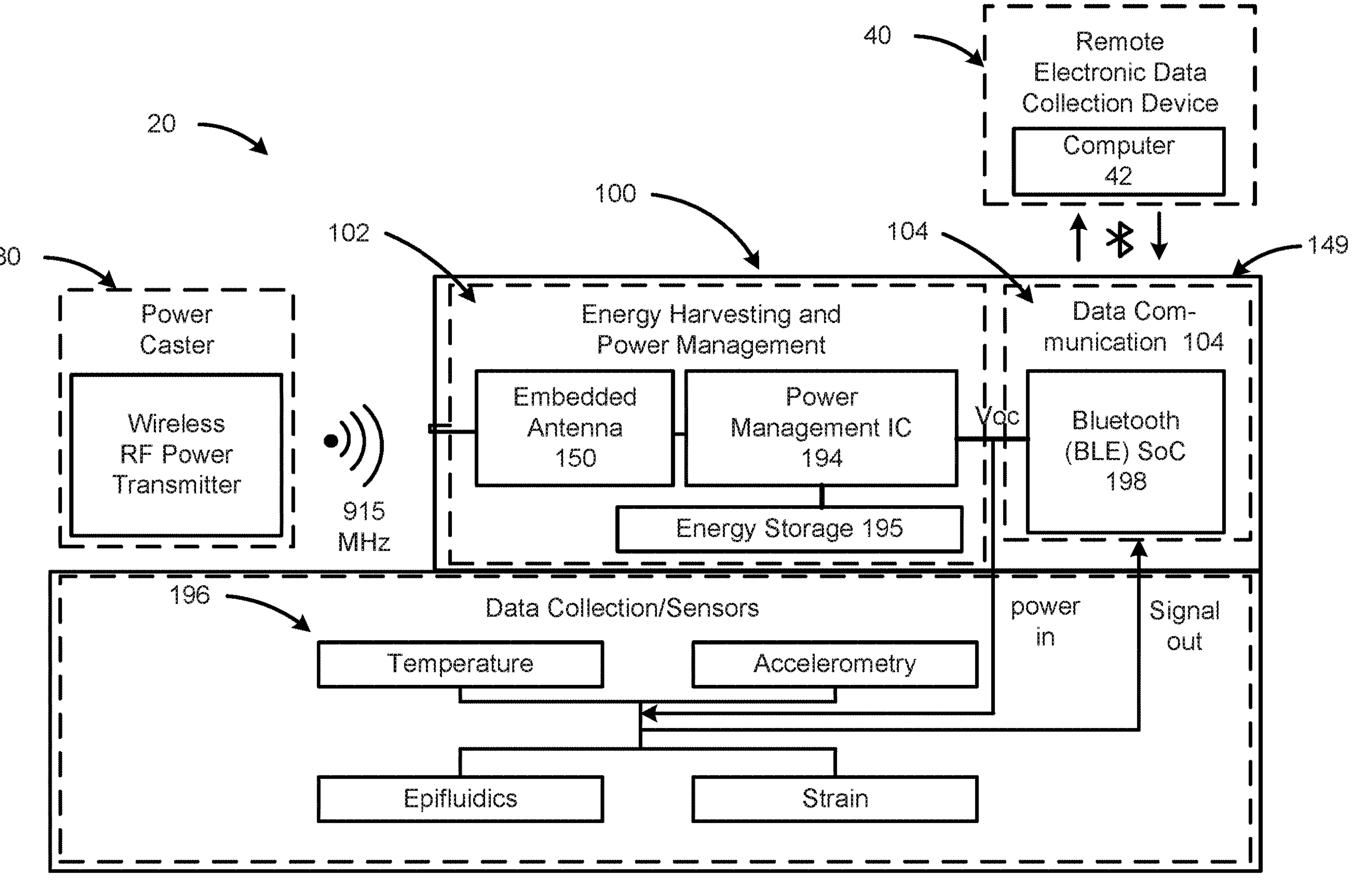
FIG. 9 is a block diagram of a system according to the present disclosure, particularly a healthcare monitoring and/or diagnostic system, which comprises a three-dimensionally printed sensing article comprising electronic components, such as wireless power receiving (harvesting) components, wireless communication components and electronic data collection (sensing) components.
Figure 10:
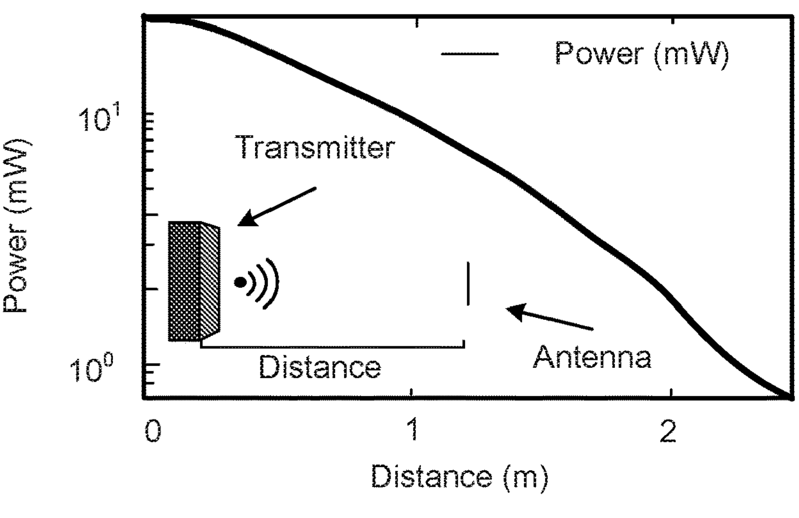
FIG. 10 is a graph of power (milliwatts) as a function of distance (meters) between the power castor/transmitting device and an antenna of a sensing article.

Referring now to FIGS. 8-10, applied together with the foregoing description and figures, the sensing article 100 provides a robust energy harvesting platform device 102, comprising an antenna 150 and other electronic components 149 comprising a power management integrated circuit 194 and an energy storage device 195 (e.g. supercapacitor, battery) to power further electronic components 149 which may comprise data collection sensors 196 and a short-range wireless communication transmitter and receiver device 104 (e.g., 10 meters or less) comprising a Bluetooth-enabled system-on-a-chip (SOC) 198 over a distance of a few meters (see FIG. 10) without the need for a battery.

The electronic components 149 are embedded in the 3D printed sensing article 100, and more particularly the 3D printed electronic enclosure 160, using discrete nodes (e.g. 170*b*, 170*d*, 170*f* and 170*h*) with a laser structured, ultra-flexible circuit substrate (e.g. 180, 184, 188) to maintain favorable mechanical properties. These electronic components 149 are embedded into the 3D printed sensing article 100, and more particularly the 3D printed electronic enclosure 160, in a one-piece monolithic platform, simplifying the production process using methods compatible with reel-to-reel manufacturing, allowing for rapid scalability. FIG. 8 shows the integration and relative locations of the electronic components 149 including the antenna 150 and other electronic components 149 embedded into the 3D printed sensing article 100, and more particularly the 3D printed electronic enclosure 160, which has a high tolerance for strain. A high-level operational schematic of the system 20 is shown in FIG. 9. The system 20 harvests RF power from a commercially available 915 MHz power caster 30. The energy is converted via a rectifier to direct current (DC) power and is stabilized by a power management device 102 that enables long-range functionality even when the power harvested is not constant. The energy is used to power the Bluetooth SOC 198 and other active electronic components 149 including the sensing modalities. Data is collected from sensing nodes placed strategically in the 3D printed sensing article 100, and more particularly the 3D printed electronic enclosure 160, and information is streamed to a Bluetooth-enabled device (e.g. computer 42) for storage and analysis. Sensing capabilities include sensors 196 such as a sub-millikelvin resolution temperature sensor, a relative humidity sensor with 2% accuracy, low noise inertial measurement unit, and 3D printed strain gauge. With low-power, highly miniaturized node footprints that are less than 6 mm in diameter, an imperceptible visual and mechanical feel may be achieved, while attaining high-fidelity signal recordings through a low impedance interface to the skin. To characterize and qualify the mechanical and chemical properties of the article/components for continual use on patients, a benchtop platform may be used to determine the mechanical characteristics of complex designs as well as long-term robustness before clinical trials through accelerated stress tests in physiological solutions. Data collected using this system 20 will guide design considerations to improve the longevity of the article/components and enhance the robust mechanical characteristics needed for long-term data acquisition.

The 3D printed, wearable, electronic, sensing article 100 is highly customizable with respect to sensing modalities and demonstrated sensing modalities include, accelerometry, temperature, and skin humidity. Preliminary testing has demonstrated a robust ability to acquire clinical-grade data streams over an extended period. Preliminary measurements of core body temperature, local skin humidity, and trunk motion have been collected using prototyped articles.

Figure 11:
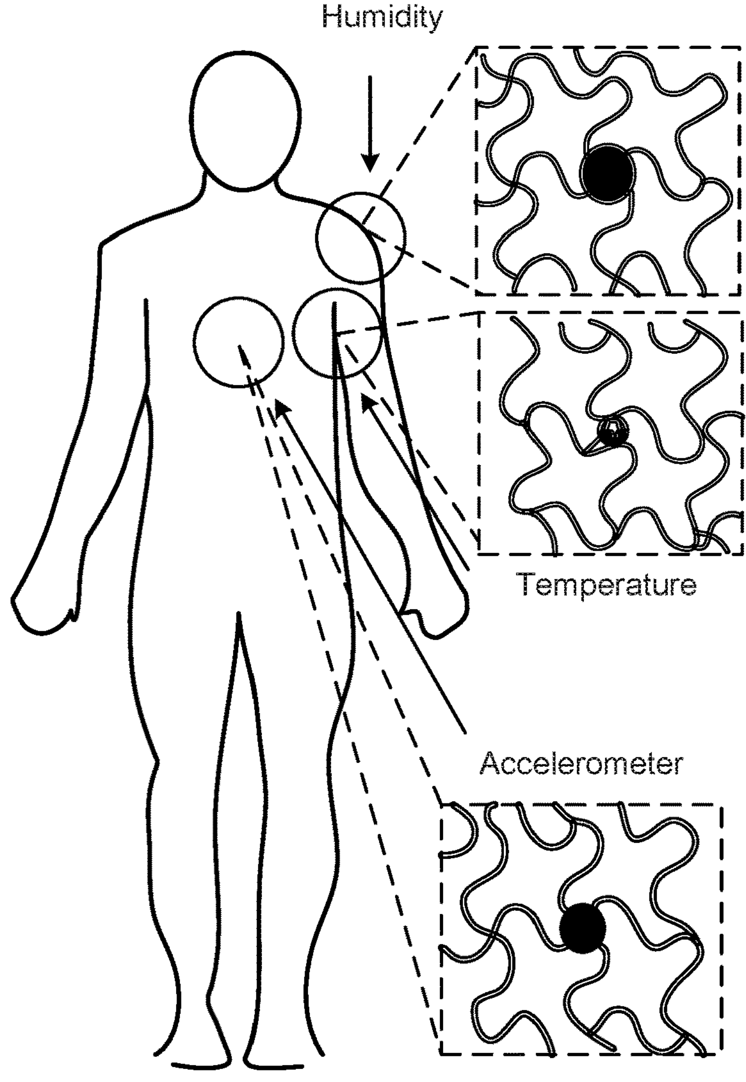
FIG. 11 is a sensing modality/component location map for electronic data collection (sensing) components of one or more three-dimensionally printed sensing articles.
Figure 12:
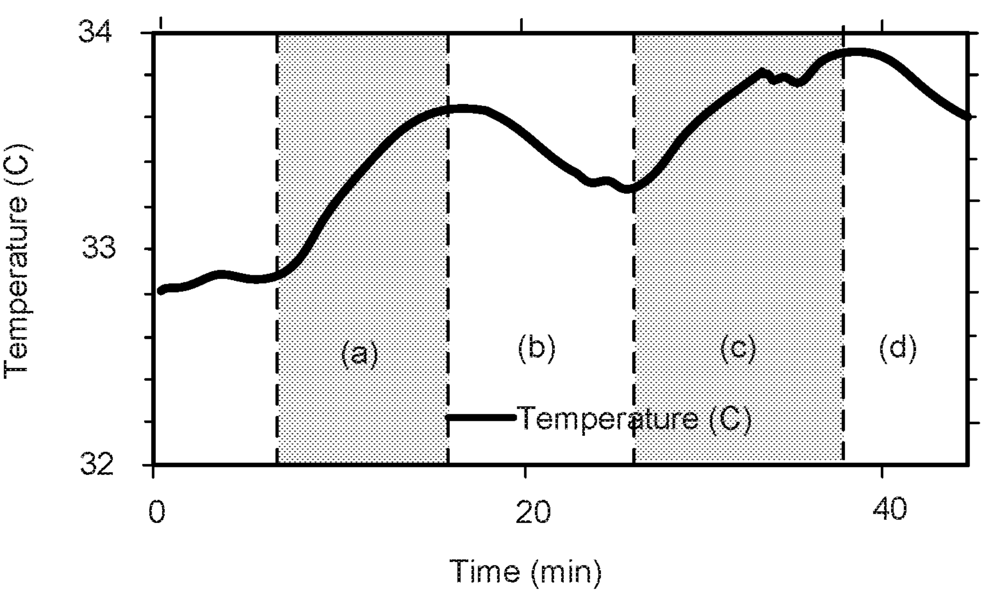
FIG. 12 is a graph of temperature (degrees Celsius) as a function of time (minutes) for sensitivity and temporal resolution of an electronic data collection (sensing) component comprising a high-fidelity temperature sensor.
Figure 13:
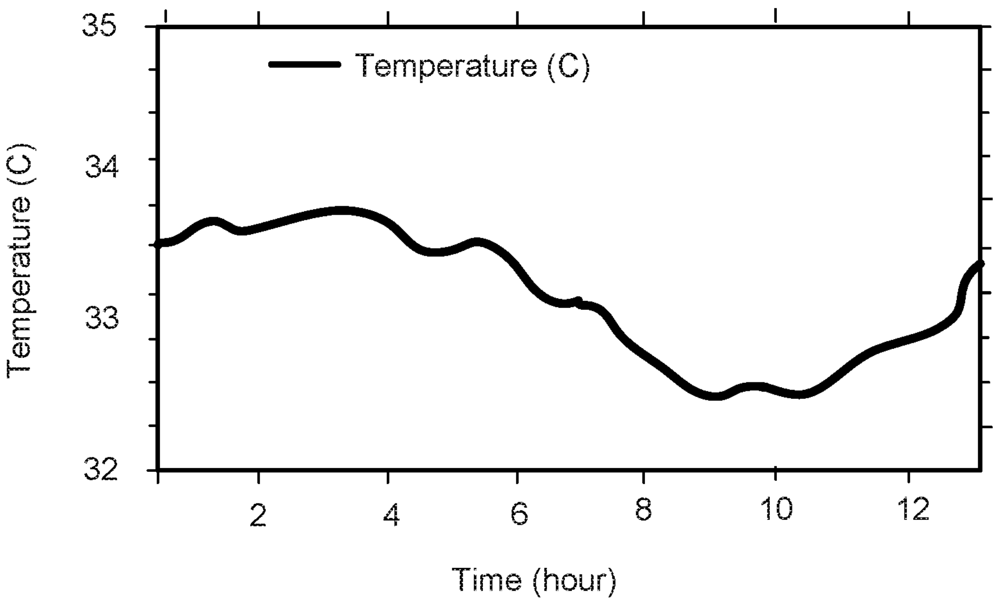
FIG. 13 is a graph of temperature (degrees Celsius) as a function of time (hours) for the electronic data collection (sensing) component comprising the high-fidelity temperature sensor showing circadian rhythm.

FIG. 11 shows some of these sensing modalities embedded in the article 100. The ultra-sensitive, low powered temperature sensor that features a 0.004 C resolution over the physiological range for surface body temperature in the under-arm. The mathematical model used for data correlation provides a less than 1% difference between theoretical and experimental system values, yielding high confidence in the data captured by this system. FIG. 12 shows the responsiveness and sensitivity of the sensor. In this experiment, the subject wore the article for 50 minutes during which they performed 8 minutes of light activity (zones (a) and (c)) followed by 10 minutes of rest (zones (b) and (d)). From the data, periods of heighted activity may be discerned and changes in steady-state body temperature after each sequential period of activity. In FIG. 13, the subject wore the article 100 for 13 hours, from 6 pm to 7 am. In this experiment, clear periods of heighted activity denoted by short-term increases in recorded temperature values were observed. The long-term trend of the data indicates the ability of the sensors to detect subtle changes in homeostasis such as the circadian rhythm.

Figure 14:
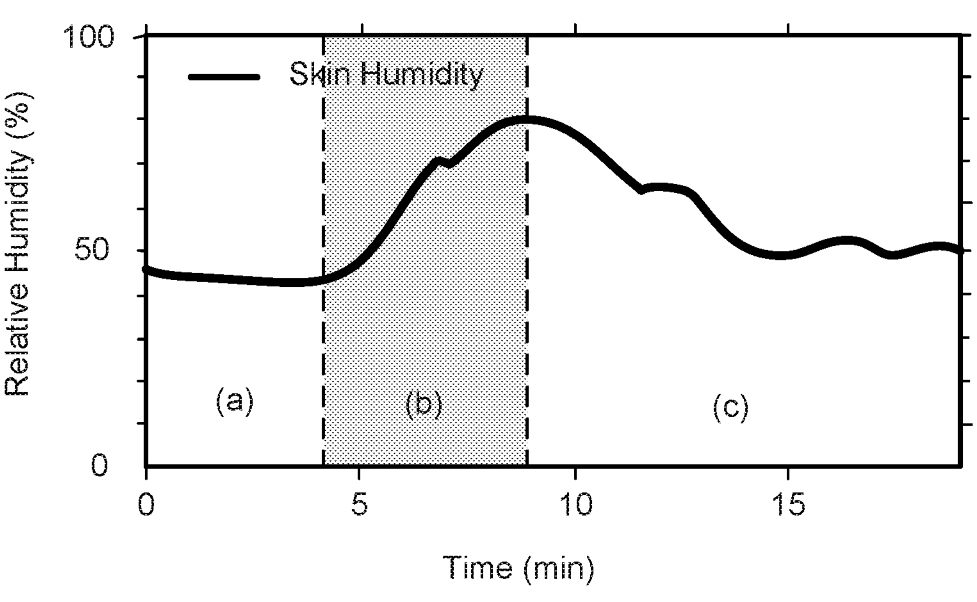
FIG. 14 is a graph of skin humidity (%, percent) as a function of time (minutes) for an electronic data collection (sensing) component comprising a skin humidity sensor.

Relative skin humidity is another physiological parameter that may be monitored to identify the onset of health concerns and acute physiological events. The data can also be used to monitor patient activity in conjunction with temperature and acceleration, while allowing for unique insight into previously unmeasured physiologies that could supplement the evaluation of patient health and activity. Increases in skin humidity and perspiration may aid in the detection of acute illness and provide semi-quantitative values of a patient's physical strain during activity. To monitor these characteristics, a low-power, highly miniaturized relative humidity sensor situated on the distal region of the upper shoulder may be used. The sensor node, which is 5 mm in diameter, utilizes 3D-printed topologies to allow for a localized influx of air to the sensor without compromising the electronics embedded in the article 100. Initial testing revealed high responsiveness of the sensor platform located on the distal portion of the shoulder. During the experiment depicted in FIG. 14, the subject wore the system for 20 minutes, in which they began by establishing a baseline during a 3-minute resting phase (zone (a)), performed activities including moderate walking and climbing stairs (zone (b)) for 6 minutes, and then rested again (zone (c)). The system demonstrated enhanced capabilities for detecting periods of heightened exercise.

Figure 15:
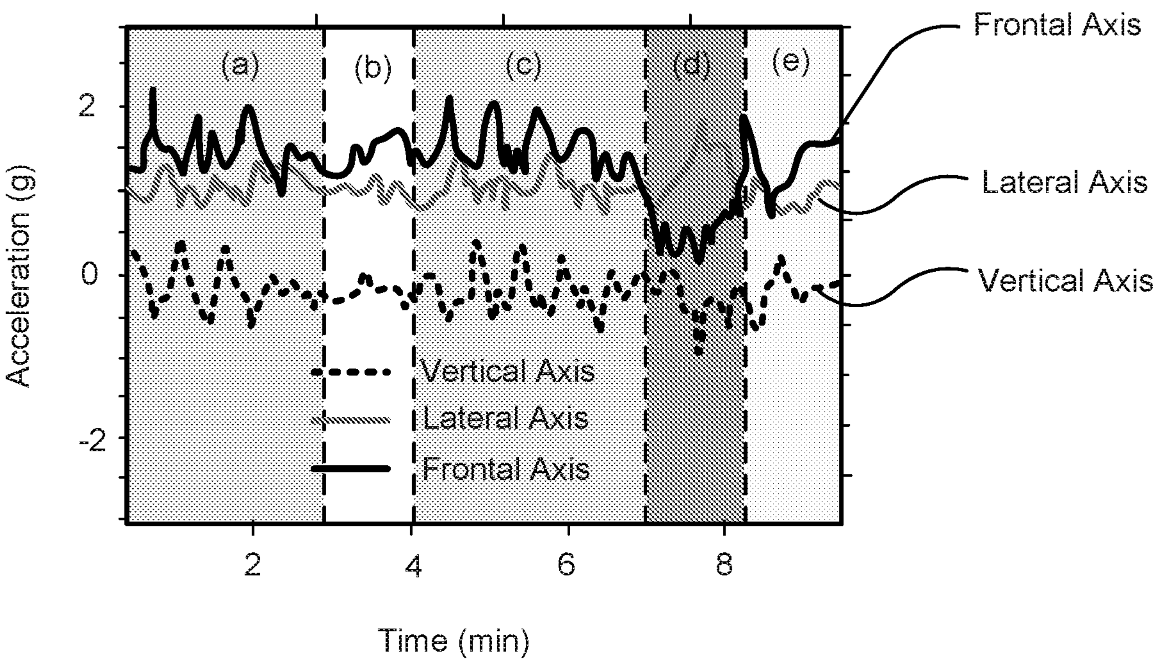
FIG. 15 is a graph of acceleration (g-force) as a function of time (sec) for an electronic data collection (sensing) component comprising an accelerometer.

Additionally, accelerometry has been demonstrated, as it will provide the meta data needed to analyze gait. A low-power accelerometer unit has been tested to measure trunk motion using the article 100. Our accelerometer platform is 5 mm in diameter and is embedded in a fixed orientation, enabling robust acceleration measurements in axis orientations that are temporally consistent. Preliminary data for this system is displayed in FIG. 15. In this experiment, the subject wore the sensing platform attached to their trunk (i.e. torso), and then performed 3 seconds of walking (zone (a)) followed by a 180 degree turn (zone (b) and 3 additional seconds of walking (zone (c)). The subject then knelt forward (zone (d)) and then returned to their original standing position (zone I). From the data, periods of activity could be distinguished and it could be determined when the subject knelt and stood up from changes in the lateral and vertical axis acceleration. The sensitivity of this modality, paired with the intimate epidermal contact, may provide clinicians and statisticians with the high-quality data needed to perform frailty analysis for this study.

Thus, a wireless, battery-free, 3D printed sensing article 100 suitable for recording high-fidelity, clinical-grade, and continuous data streams to allow for advanced diagnosis using an imperceptible form factor is provided. While the data shown here was recorded on single mode devices, it is feasible to combine the modalities into one platform to obtain a holistic view of patient activity and physiology over time.

To provide the three-dimensionally printed, wearable, electronic, sensing article 100, which is also wireless, battery-free, non-invasive and personalized to the body of the wearer, highly scalable digital manufacturing techniques may be utilized, which further allow for rapid reconfiguration of the sensing system based on target biomarker which may be personalized to the individual subject in the study. Critical to a personalized sensing article 100 that is applied epidermally is an intimate fit of localized sensors directly at the site of interest. This ensures minimal motion artifacts which are induced by relative motion of sensor and epidermis. Moreover, the article 100 may be applied without use of an adhesive, and hence not suffer from associated poor chronic sensor performance after renewal of the epidermis, which occurs depending on subject, after 1-2 weeks and irritation that occurs even with the use of clinically tested adhesives.

Figure 16A:
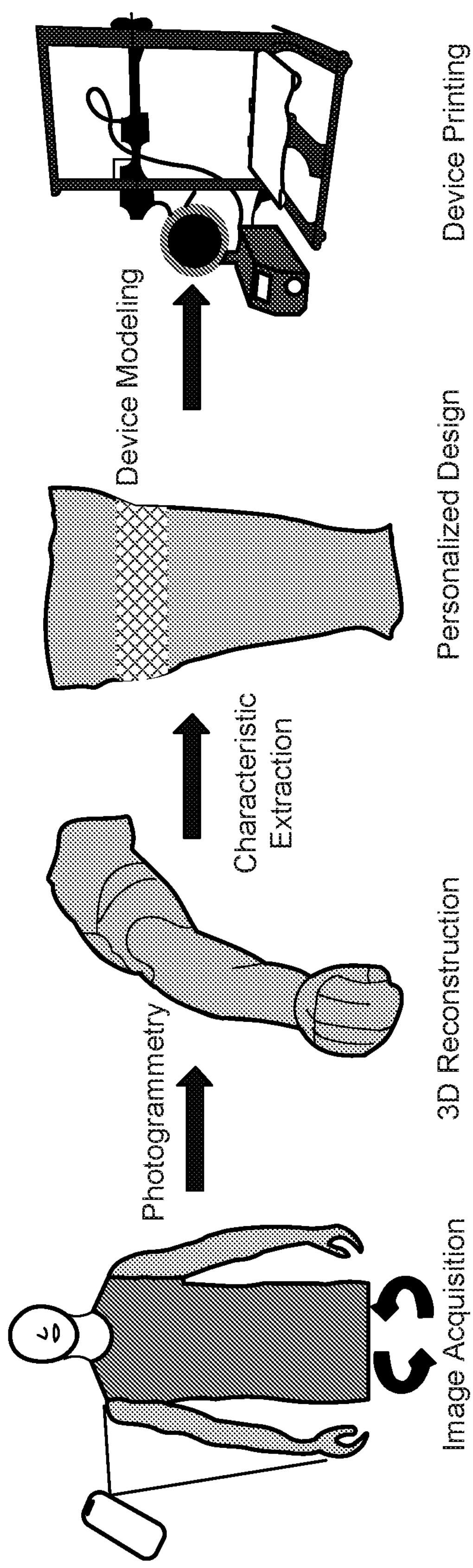
FIG. 16A is a sequence diagram showing three-dimensional digital data mapping of the surface of an appendage of a human body, particularly by photogrammetric mapping, to create a three-dimensional model of the surface of the appendage of the body.
Figure 16B:
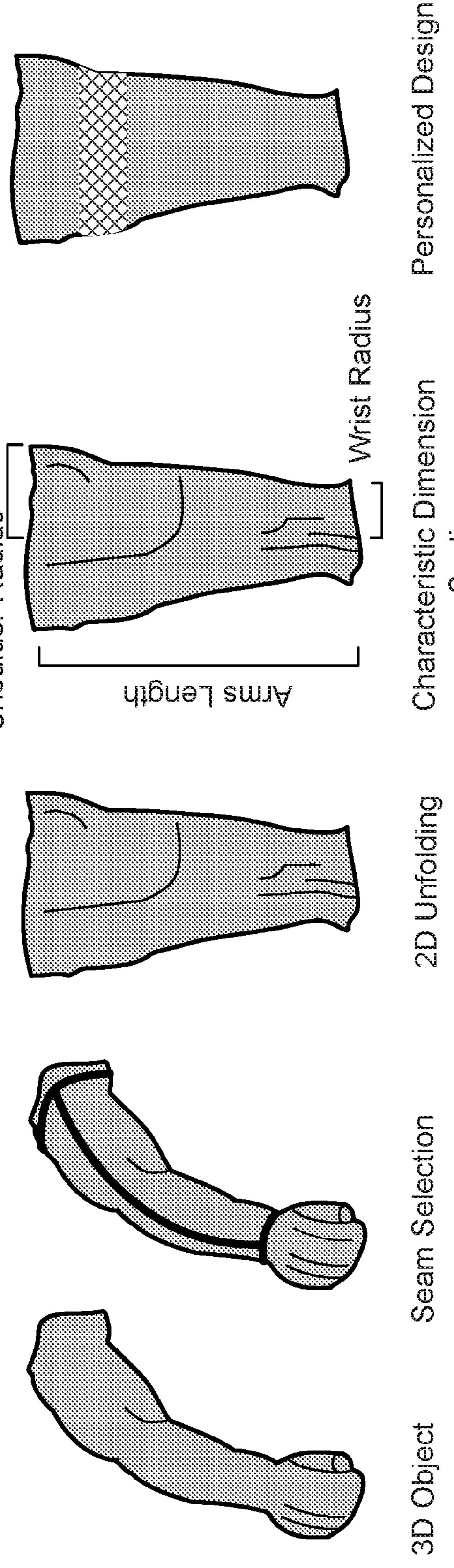
FIG. 16B is a sequence diagram showing extraction of two-dimensional physiological data of a surface of the appendage of the body from the three-dimensional data/model.

Referring to FIGS. 16A-16B, such depict formation of an article 100, and more particularly a base 110 particularly in the form of the mesh 112, which is personalized to the body 10 of the wearer. As shown, to generate the personalized article 100, at least a surface of a selected region of a body 10 of a particular (unique) wearer of the article 100 is three-dimensionally, digitally mapped. For example, as shown, at least the surface of an appendage 12 (e.g. arm) of the body 10 of the particular wearer may be obtained by photogrammetric mapping, which may simply be referred to as photogrammetry. Other 3D digital mapping techniques, such as magnetic resonance imaging (MRI) and computerized tomography (CT) scanning, may also be utilized as appropriate. Next, a 3D digital model (mathematical representation) of the surface of the selected region of the wearer's body 10 is generated from data of a dataset of the 3D mapping. Data from the dataset of the 3D digital model of the surface of the selected region of the wearer's body 10 is then manipulated, via software (particularly by unfolding the data of the 3D model dataset), to generate a two-dimensional (2D) template for three-dimensional printing.

Three-dimensional printing (e.g. fused filament fabrication (FFF); fused deposition modeling (FDM)) of the base 110 of the article 100 is next performed, from the two-dimensional template, where the base 110 of the article 100 comprises the mesh 112, which is formed of an elastomeric polymer composition. By virtue of being formed of the elastomeric polymer composition, the base 110/mesh 112 is flexible, soft and stretchable (elastic), whereby the base 110/mesh 112 is conformable (e.g. circumferentially) to changes in body shape of the wearer's body 10, and more particularly the surface of the selected region of the body 10 of the wearer of the article 100, during movement. Moreover, the individually tailored fit results in at least substantially perfect conformality to the wearer's body 10, enabling high-fidelity and chronic biodata acquisition that is adhesive free, which may enable continuous attachment to the wearer's body for periods of duration at least a week (e.g. at least 2 weeks).

The elastomeric polymer composition may be at least one of a synthetic elastomeric polymer composition and a thermoplastic elastomeric polymer composition, which may comprise, essentially consist of, or consist of, at least one elastomer, which may comprise, essentially consist of, or consist of at least one of a synthetic polymer and a thermoplastic polymer.

The elastomeric polymer composition may have a glass transition temperature (Tg) below 23° C. and be, at most, 50% crystalline (i.e., the composition contains an amorphous phase of 50% or greater, up to 100% amorphous phase). Additionally, or alternatively, the elastomeric polymer composition may be a polymer composition that has an elongation at 23° C. of at least 100%, and which, after being stretched to twice its original length and being held at such for one minute, may recover in a range of 50% to 100% within one minute after release from the stress. More particularly, the elastomeric polymer composition may recover in a range of 75% to 100% within one minute after release from the stress, and even more particularly recover in a range of 90% to 100% within one minute after release from the stress. Additionally, or alternatively, the elastomeric polymer composition may have the following mechanical properties.

| Mechanical Property | Test Method | Value (range) |
|---|---|---|
| Shore A Hardness | ASTM D2240 | 60-100 Shore A |
| Tensile Strength | ASTM D412 | 2-60 Mpa |
| Elongation @ Break | ASTM D412 | 400-800% |

Note:
The foregoing ASTM test methods is the most recent test methodadopted by the ASTM as of the data of filing the application.

In one particular embodiment the elastomeric polymer composition may be a thermoplastic urethane (TPU) elastomeric polymer composition, wherein the at least one elastomer may be a thermoplastic urethane (TPU) elastomer. The thermoplastic urethane (TPU) elastomer may be supplied by, for example, NinjaFlex by NinjaTek, Varioshore by Colorfabb, X60A by Diabase Engineering.

Thus, the present disclosure provides an article 100 that can be created using a set of smart phone pictures and photogrammetry to yield body shape to automatically create a printable, soft and wearable mesh design that can house a cohort of sensors, radio frequency (RF) energy harvesting antenna for indefinite operation at distance, and Bluetooth radio to relay sensor information.

The article 100 may provide intimate epidermal contact that enables high-fidelity extraction of biophysical parameters such as, but not limited to, temperature with mK resolution, 9 axis inertial measurement unit data and skin humidity to detect sweat onset before liquid sweat secretion. Coupled with these biophysical parameters will be an inline electrochemical sweat detection platform that enables facile extension to broad classes of biomarkers using rapid, label-free, highly sensitive all-printed sensor arrays.

As shown in FIGS. 17A-17G, sensing article 100 may include a microfluidic structure 199, particularly including a microfluidic channel 200 in a microfluidic channel enclosure 210. Similar to the antenna 150, the microfluidic channel 200 may have a curvilinear (serpentine/oscillating) repeating wave shape 204 which may also extend in a microfluidic channel longitudinal direction 202, which is also a transverse direction relative to the sensing article longitudinal direction 158. When sensing article 100 is disposed on the body (e.g. extending/wrapped around an appendage 12), the microfluidic channel longitudinal direction 202 may extend along the longitudinal (proximal-distal) direction 14 of the appendage 14, while the sensing article longitudinal direction 158 extends in a circumferential direction around the appendage 12. As shown, the wave shape 204 is formed by a plurality of alternating, reverse semi-circular (e.g. in a range of 180-200 degrees) segments 206 arranged adjacent one another end to end in the microfluidic channel longitudinal direction 202. The wave shape 204 may provide a channel 200 having a desired overall length which is less than the corresponding longitudinal length, thus reducing longitudinal packaging.

Figure 17A:
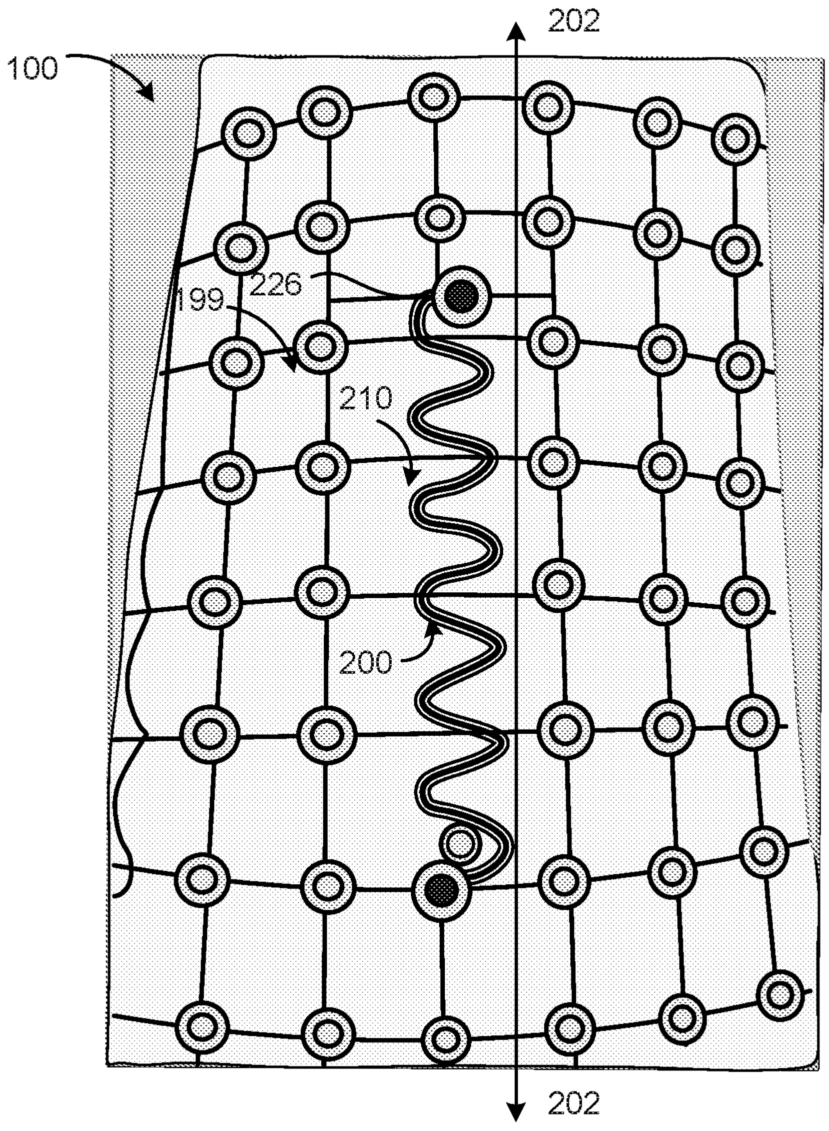
FIG. 17A is a top view of a three-dimensionally printed sensing article, including a microfluidic structure, particularly including a microfluidic channel (for eccrine sweat collection) in a microfluidic channel enclosure, disposed in three-dimensional form on the body, particularly a forearm and extending around the proximal-distal axis.
Figures 17B, 17C, 17D, 17E, 17F:
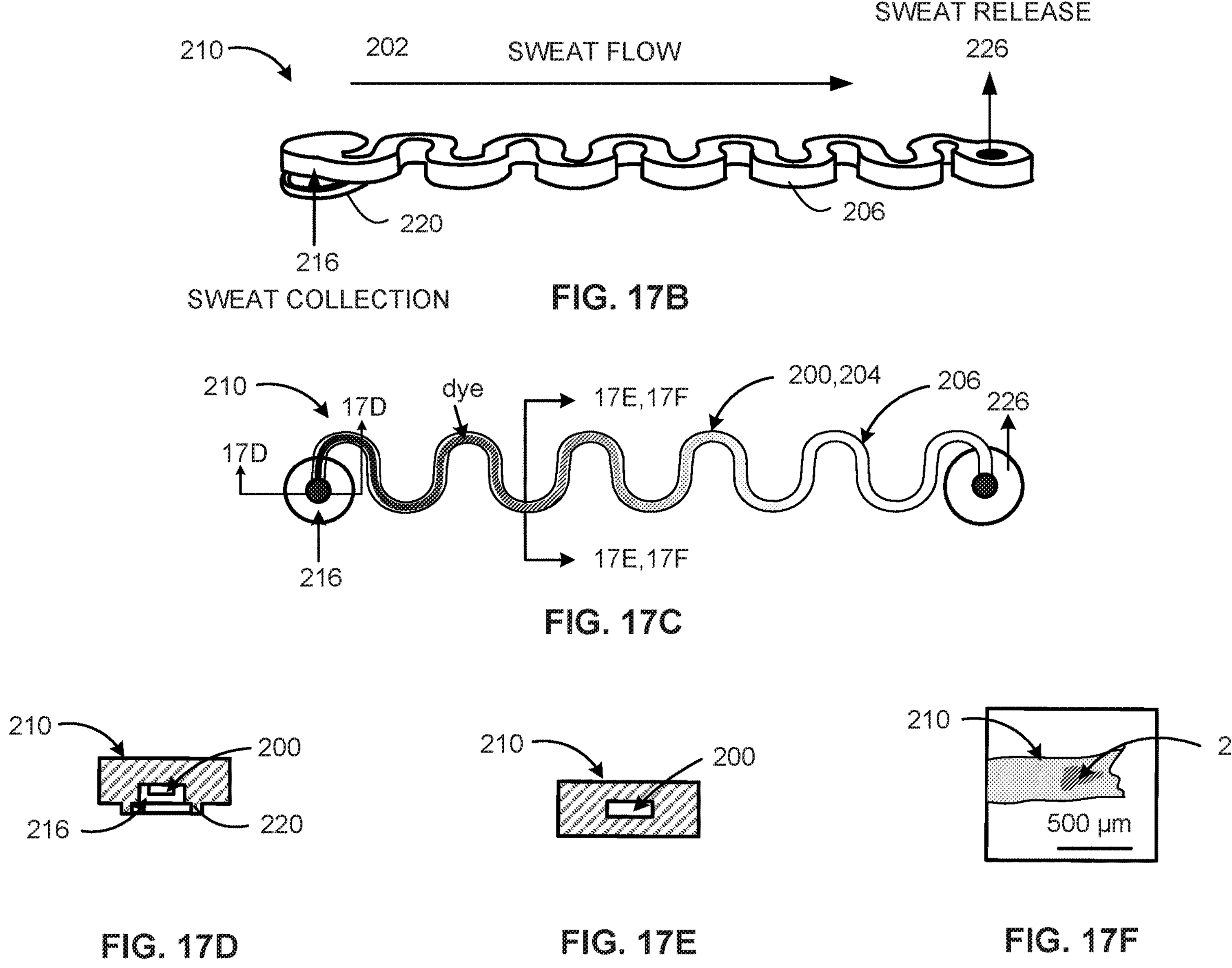
FIG. 17B is a side view of the three-dimensionally printed microfluidic channel structure of the sensing article of FIG. 17A showing collection and release of sweat.
FIG. 17C is a top view of the of the three-dimensionally printed microfluidic structure, including the microfluidic channel in the microfluidic channel enclosure, of the sensing article of FIG. 17A.
FIG. 17D is a cross-sectional view of the three-dimensionally printed microfluidic structure, including the microfluidic channel in the microfluidic channel enclosure, of FIG. 17C taken along section line 17D-17D.
FIG. 17E is a cross-sectional view of the three-dimensionally printed microfluidic structure, including the microfluidic channel in the microfluidic channel enclosure, of FIG. 17C taken along section line 17E-17E.
FIG. 17F is cross-sectional (photographic) view of the three-dimensionally printed microfluidic structure, including the microfluidic channel in the microfluidic channel enclosure, of FIG. 17C taken along section line 17F-17F.
Figure 17G:
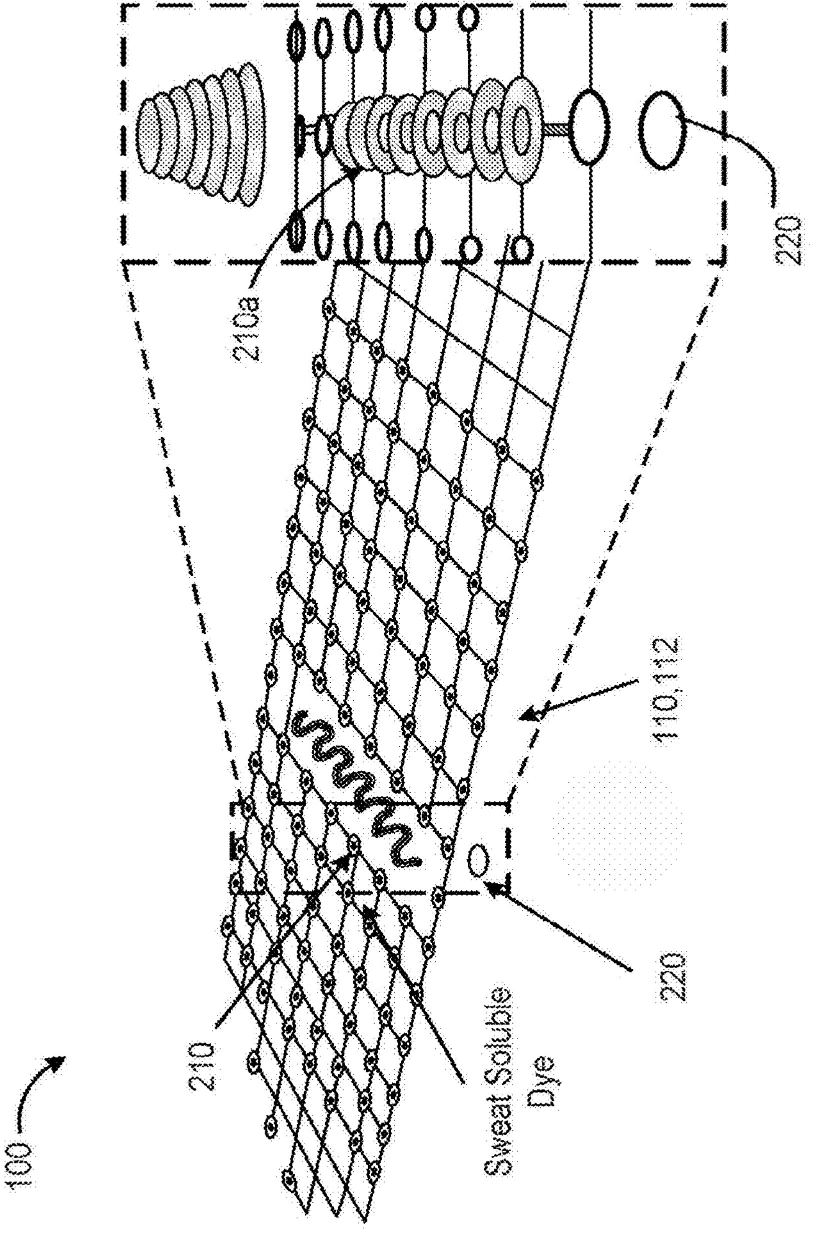
FIG. 17G is an exploded view of the microfluidic structure of the sensing article.

The microfluidic channel 200 may have a cross-sectional area which is defined by three-dimensionally (3D) printed microfluidic channel enclosure 210 of the sensing article 100 (shown divided in FIG. 17G as a lower enclosure 210*a* and an upper enclosure 210*b* and an annual rib/O-ring 220 for purposes of illustration).

The microfluidic channel enclosure 210 may be formed of the same 3D printed elastomeric material as the base 110/mesh 112 and thus formed as one-piece with the base 110/mesh 112. As with the electronic enclosure 160, the microfluidic channel enclosure 210 may be in the same plane as the strut segments 116 of the base 110/mesh 112, in which case the strut segments 116 are connected laterally to a vertical side of the enclosure 210, and to not extend underneath the enclosure 210. Alternatively, as with the electronic enclosure 160, the microfluidic channel enclosure 210 may be disposed on top of (i.e. raised above/overlie) the strut segments 116 of the base 110/mesh 112, in which case the strut segments 116 are connected to a bottom of the enclosure 210. Moreover, it should be understood that, in certain embodiments, certain strut segments 116 may be connected laterally to the vertical side of the enclosure 210, while other strut segments 116 may be connected to the bottom side of the enclosure 210.

The microfluidic channel 200 may have a circular cross-sectional shape (i.e. transverse to the flow direction), in which case the channel 200 may be understood as being cylindrical, or other cross-sectional shape, such as polygonal (e.g. rectangular cross-sectional shape). Similarly, the microfluidic channel enclosure 210 may have a circular cross-sectional shape (e.g. annular), in which case the enclosure 210 may be understood as being cylindrical, or other cross-sectional shape, such as polygonal (e.g. rectangular frame cross-sectional shape). Thus, the microfluidic channel 200 or the microfluidic channel enclosure 210 may be defined by a circular (cylindrical and/or annular) or polygonal (rectangular frame) wall/surface of the article 100.

The microfluidic channel 200 has a (sweat collection) inlet 216 and a (sweat collection) outlet 226 disposed at opposite ends of the channel 200. The inlet 216 faces the skin, while the outlet 226 faces opposite the inlet 216 away from the skin. The channel 200 has a length from the inlet 216 to the outlet 226 in range of 10-100 mm, and a channel (cross-sectional) area in a range of 0.2-0.4 $mm^2$, and preferably of a uniform cross-sectional area along its length. The wave shape 204 of the microfluidic channel enclosure 210 may increase the stiffness/rigidity of the microfluidic channel enclosure 210, as compared to a rectilinear channel enclosure, particularly to inhibit deformation and change of the cross-sectional area of the channel 200 under pressure.

To better ensure intimate skin contact and form a better seal, a 3D printed elastomeric annular rib/O-ring 220 (see e.g. FIGS. 17D and 17G) may be disposed between the skin (directly on the skin) of the subject and the inlet 216 to the channel 200. The elastomeric annular rib/O-ring 220 may have a (rib) height in a range of 0.1 mm to 2.5 mm, more particularly in a range of 0.3 mm to 1.5 mm and even more particularly in a range of 0.5 mm to 1.2 mm. The elastomeric annular rib/O-ring 220 may have a (rib) width in a range of 0.1 mm to 2.5 mm, more particularly in a range of 0.3 mm to 1.5 mm and even more particularly in a range of 0.5 mm to 1.2 mm. The elastomeric annular rib/O-ring 220 may have a diameter in a range of 2 mm to 8 mm and more particularly 3 mm to 6 mm.

While the microfluidic channel enclosure 210 may be formed, particularly after the lower enclosure 210*a* is formed, a colorimetric dye may be applied to the 3D printed surfaces forming the microfluidic channel 200 in be allowed to dry prior to formation of the upper enclosure 210*b* in situ on the lower enclosure 210*a*.

Figure 17H:
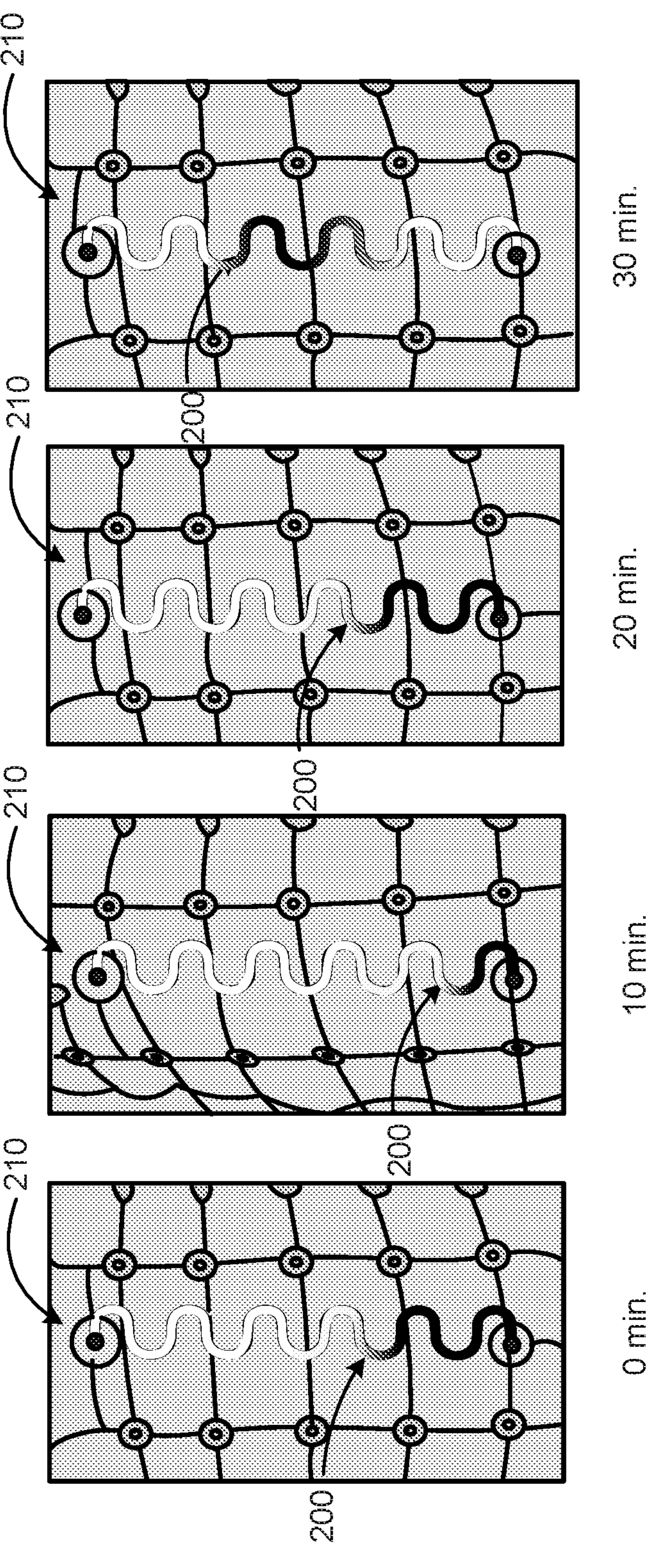
FIG. 17H is a sequence diagram showing sweat collection from a human body within a three-dimensionally printed microfluidic channel at 10 minutes intervals of 30 minute time period, particularly during callisthenic exercise.
Figure 17J:
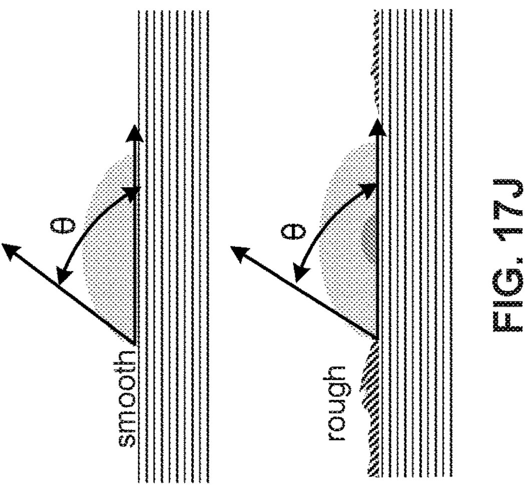
FIG. 17J is a view of contact angle of water disposed on smooth and rough surfaces of three-dimensionally printed thermoplastic polyurethane for the sensing article.
Figure 17L:
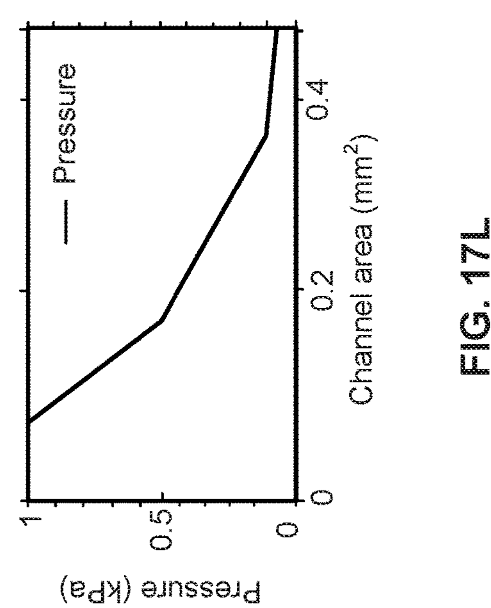
FIG. 17L is a graph of inlet pressure (kilopascals) to induce fluid (e.g. sweat) flow therethrough as a function of microfluidic channel area (square millimeters)
Figure 17I:
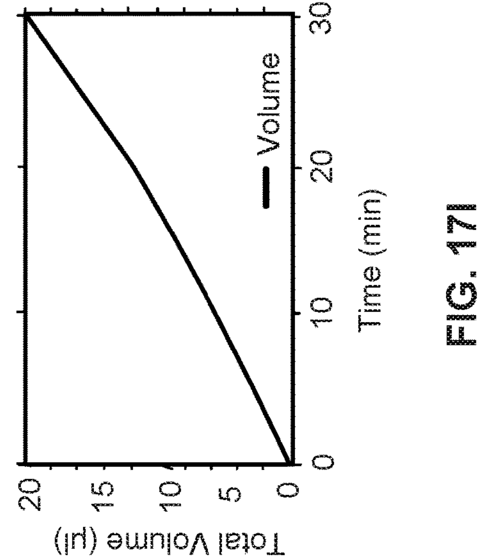
FIG. 17I is a graph of total sweat volume (microliters) collected as a function of time (minutes) for the 30 minute time period.

During operation, eccrine sweat (i.e. sweat from the eccrine glands) may be collected into the microfluidic channel 200. As shown particularly by FIGS. 17C and 17H, sweat from the subject collected into the microfluidic channel 200 at the inlet 216 may then travel in the microfluidic channel 200 and then ultimately be released from the outlet 226. The dye is used to visually show the progression of the sweat in the channel 200, which can then be recorded as a function of time to determine the level to which the subject is sweating/perspiring. As shown by FIG. 17I, the volume of sweat over 30 minutes may be approximately 20 μl.

Fluid (sweat) flow into the microfluidic channel 200 may be better facilitated depending upon the contact angle, which may be represented by θ, of the fluid on the surface of the channel 200 formed of the 3D printed elastomer, such as thermoplastic urethane (TPU).

Figure 17K:
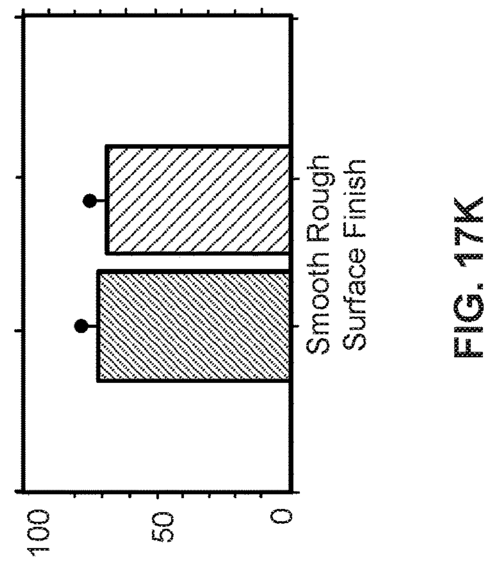
FIG. 17K is a bar graph of contact angle of water disposed on smooth and rough surfaces of three-dimensionally printed thermoplastic polyurethane for the sensing article.

Contact angle θ is a quantitative measure of the wetting of a solid by a liquid. Contact angle θ may be defined geometrically as the angle formed by a liquid at the three phase boundary where a liquid, gas and solid intersect. In terms of the thermodynamics of the materials involved, contact angle θ involves the interfacial free energies between the three phases given by the equation $\gamma LV \cos\theta = \gamma SV - \gamma SL$, where γLV, γSV and γSL refer to the interfacial energies of the liquid/vapor, solid/vapor and solid/liquid interfaces, respectively. If the contact angle θ is less than 90 degrees the liquid may be said to wet the solid. If the contact angle is greater than 90 degrees the liquid is non-wetting. A zero contact angle θ represents complete wetting. When the surface of the microfluidic channel 200 is formed with the TPU, the contact angle θ of the fluid (sweat) thereon is advantageously less than 90 degrees. The lower contact angle θ, particularly less than 90 degrees, may be understood to lower the resistance to flow of the fluid (sweat) into the channel 200. As shown by FIGS. 17J and 17K, with the TPU, the contact angle θ is in a range of 70-80 degrees, somewhat regardless of the surface finish being smooth or rough.

Given that the TPU has a contact angle θ with the fluid (sweat) which is less than 90 degrees for the surface of the microfluidic channel 200, the TPU surface may be understood to be a hydrophilic surface.

Fluid (sweat) flow into the microfluidic channel 200 may also be better facilitated depending upon the cross-sectional area of the microfluidic channel 200. FIG. 17L shows how the fluid pressure required for the sweat to enter the microfluidic channel 200 decreases as a function of increasing cross-sectional area of the microfluidic channel 200. As shown, the when the cross-sectional area of the microfluidic channel 200 increase from 0.2 to 0.4 square millimeters (mm 2), the fluid pressure required for the sweat to enter the microfluidic channel 200 decreases from 0.5 to 0.05 kPa.

Depending on the cross-sectional area of the microfluidic channel 200, when the surface of the microfluidic channel 200 is hydrophilic, the microfluidic channel 200 may exhibit capillary action with regards to uptake of the fluid (sweat). The lower the contact angle θ (the more hydrophilic the surface), the higher the capillary pressure and thus the stronger the capillary action. The capillary action is desirable as the pressure to take the fluid (sweat) into the microfluidic channel 200 will less than the pressure applied to the fluid (sweat) to expel it from the body 10.

Figures 18A, 18B:
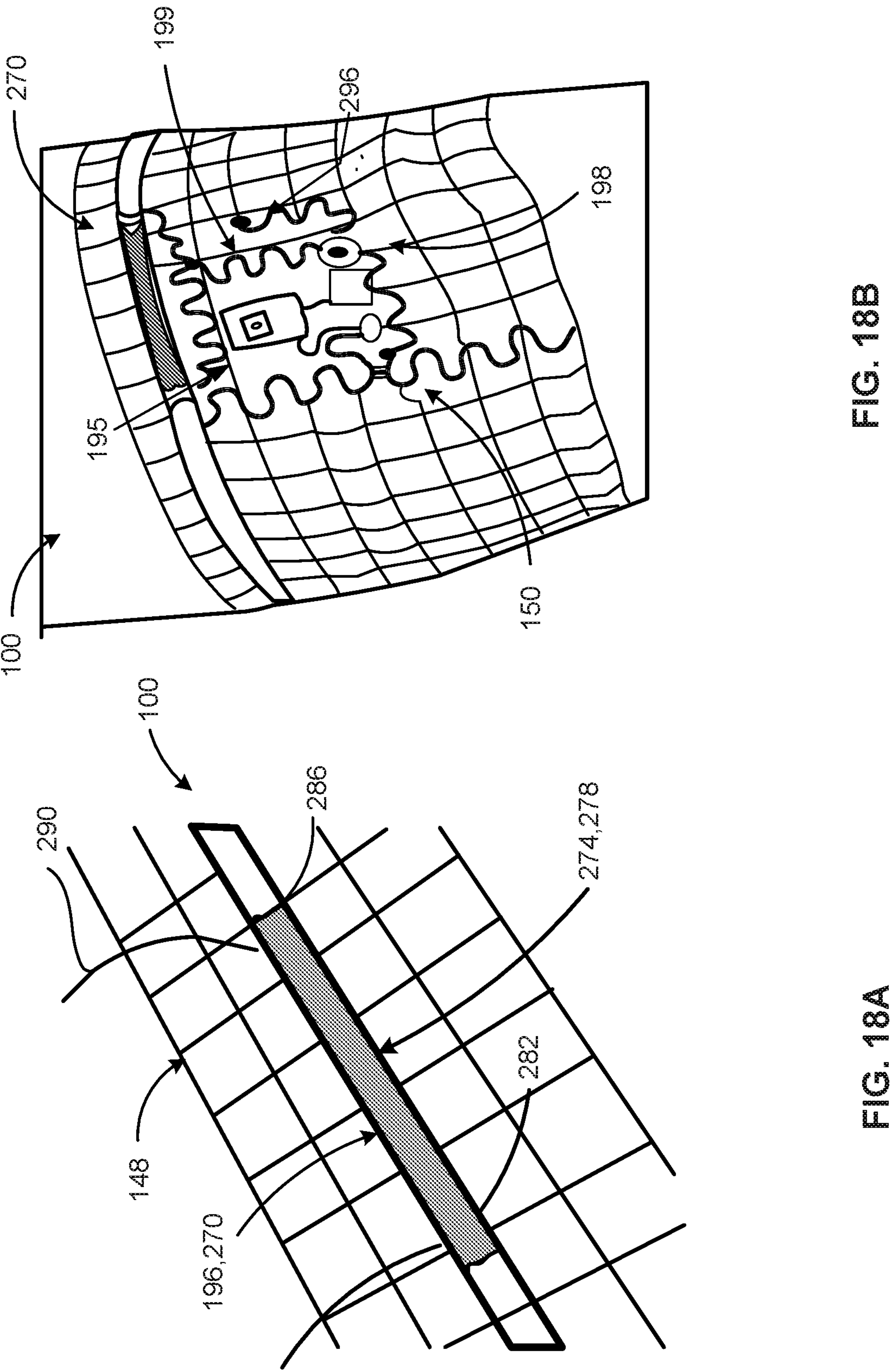
FIG. 18A is a view of an exemplary three-dimensionally printed sensing article including an electronic structure, particularly including a strain gauge structure comprising a strain gauge sensor embedded/encapsulated in a three-dimensionally printed strain gauge enclosure of the sensing article.
FIG. 18B is a view of the strain gauge structure of the three-dimensionally printed sensing article disposed on a body with other components.
Figure 18C:
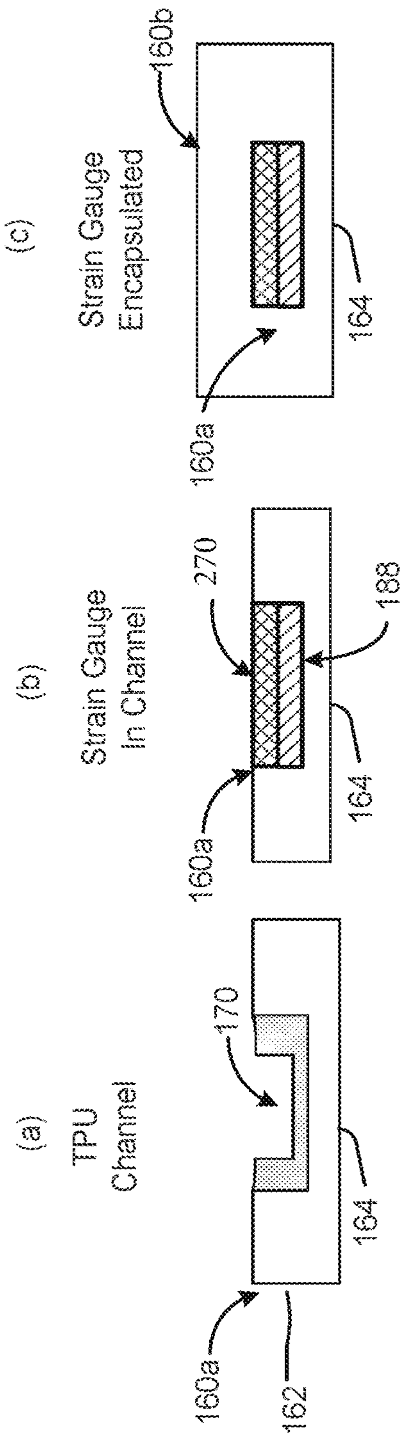
FIG. 18C are cross-sectional views of the strain gauge sensor in the strain gauge enclosure during fabrication of the sensing article.

As shown in FIGS. 18A-18C, article 100 may include another electronic structure 148, particularly another sensor 196 in the form of a wireless stain gauge sensor 270. The strain gauge sensor 270 may be formed by placing electrical conductor 188 within recess 170 of the lower enclosure 160*a*. A length portion of the electrical conductor 188 may then be removed, in which case two (end) portions 282, 286 of the conductor 188 may now be electrically disconnected from one another. Thereafter, an elongated strain element 274 formed of electrically conductive thermoplastic elastomer (e.g. thermoplastic urethane filled with an electrically conductive particulate such as carbon black) may by three-dimensionally printed in/along the recess 170 at the location of the removed conductor 188 as well as overlie the two disconnected (end) portions 282, 286 of the conductor 188, thus reestablishing electrically connectivity of the conductor 188 along the length of the elongated strain element 274. The (end) portions 282, 286 of the conductor 188 may also be coupled to leads 290 to determine electrically resistance changes at opposing ends of the elongated strain element 274 in response to strain being applied to the elongated strain element 274 (e.g. due to contraction of muscles). As shown, article 100 also may include another sensor 196 in the form of a temperature sensor 296, as well as a microfluidics structure 199.

As shown by FIG. 18C, similar to the formation of antenna 150, once the lower enclosure 160*a* is formed with recess 170, a layered electronic structure may then be disposed in the recess 170. The layered structure, may comprise electrical power (flexible metal copper) conductor 188 and strain gauge sensor 270 disposed over the comprise electrical power (flexible metal copper) conductor 188.

Figures 19A, 19B, 19C, 19D:
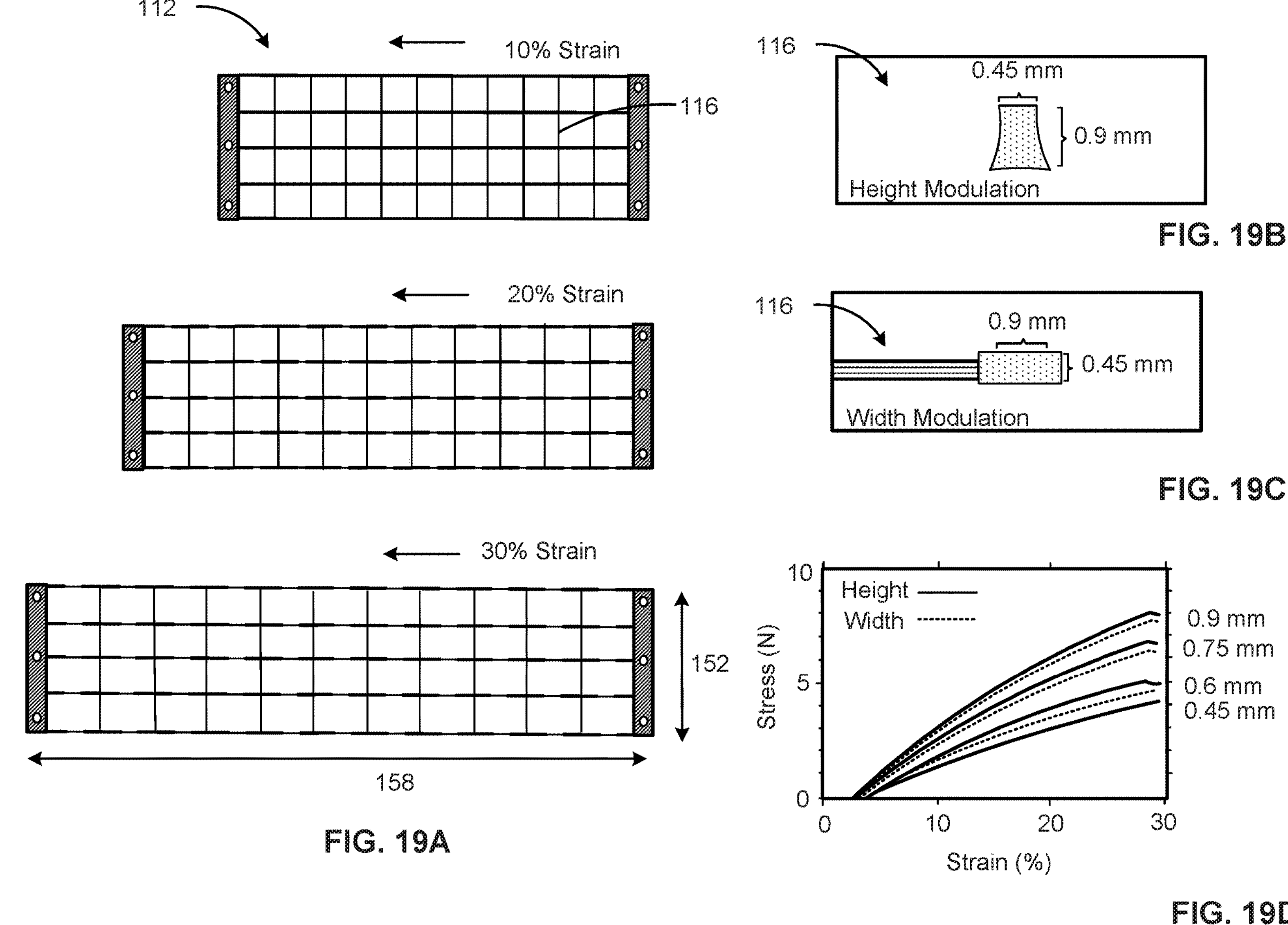
FIG. 19A is a view of a mesh structure of the sensing article in response to strains of 10%, 20% and 30% in the longitudinal direction.
FIG. 19B is a cross-sectional view of a strut of the mesh structure.
FIG. 19C is another cross-sectional view of a strut of the mesh structure.
FIG. 19D is a graph of stress versus strain curves displaying results of height and thickness modulation for the struts.

Referring now to FIGS. 19A-19D, there is shown some of the tunable bulk mechanics of the mesh. As shown in FIG. 19A, as strain increases from 10% to 30%, the struts 116 the longitudinal direction 158, the strain does not correspondingly increase in the struts 116 in the transverse direction 152. As explained, supra, such may be used to inhibit strain particularly on certain electronic components 149. FIGS. 19B and 19C shows tunability of the struts 116 by modulation of height and width. FIG. 19D shows stress versus strain curves displaying results of height and thickness modulation for the struts 116.

Figures 20, 21:
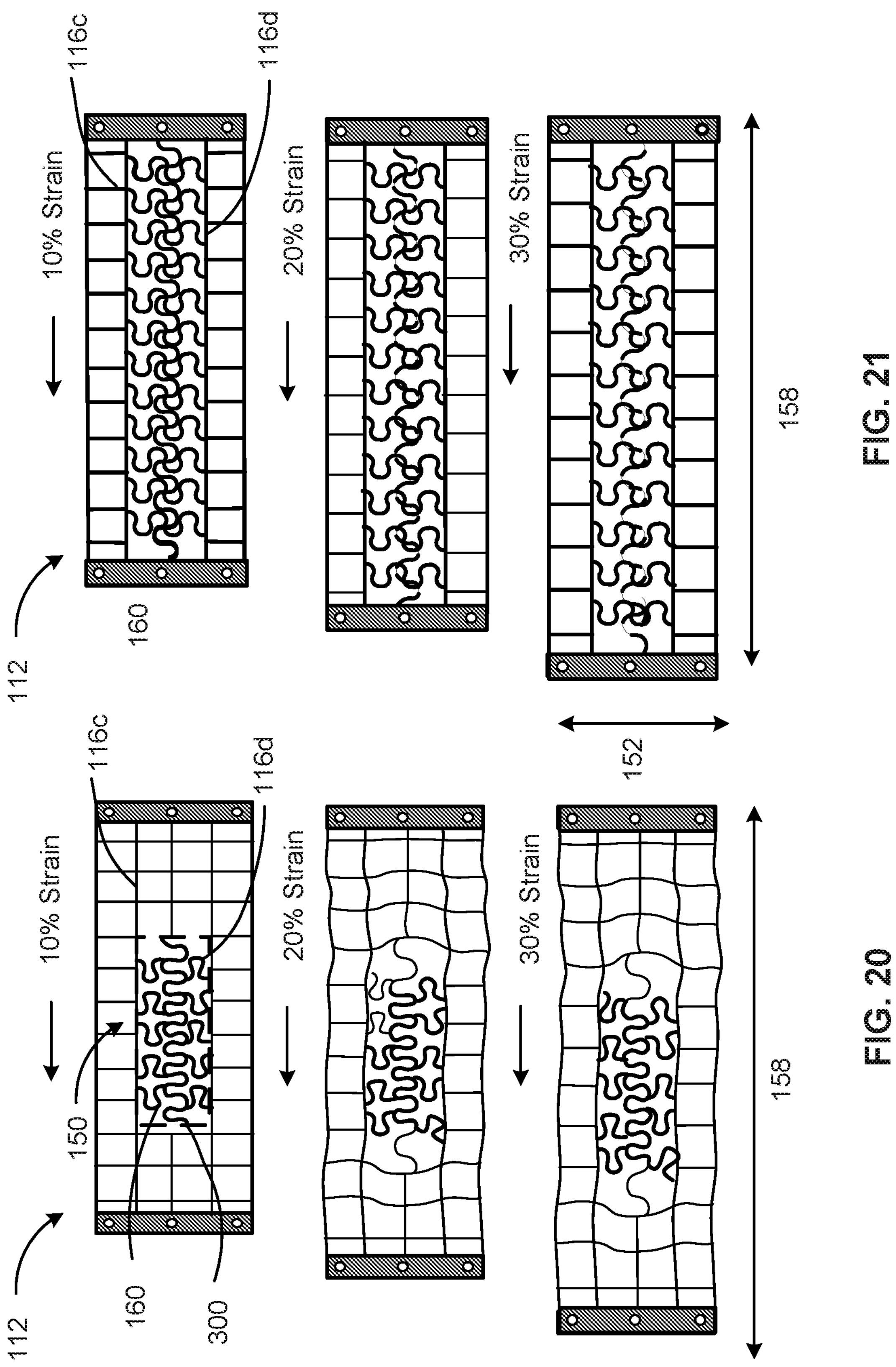
FIG. 20 is a view of a mesh structure for strain isolation of electronics.
FIG. 21 is a view of an enclosure disposed on top of the struts of the mesh structure.

As set forth, supra, it may be desirable to arrange certain electronic components 149, such as the antenna 150, with the antenna longitudinal direction being the same as the sensing article transverse direction 152 as to reduce stress on the antenna 150 which may occur in the sensing article longitudinal direction 158, particularly when the sensing article 100 is wrapped around an appendage 12. However, as shown by FIG. 20, design of the struts 116 may be used strain isolate certain electronic components 149. As shown in FIG. 20, the antenna 150 may be arranged with the antenna longitudinal direction 152 being the same as the sensing article longitudinal direction 158.

As shown in FIG. 20, the strut segments 116 are connected laterally to a vertical side 162 of the enclosure 160, and to not extend underneath the electronic enclosure 160. As shown, all the strut segments 116 directly connected to the electronic enclosure 160, i.e. within region 300, are curved strut segments 116*d* (curvilinear along their respective lengths), particularly having a semi-circular curvature arc segment (e.g. in a range of 180-200 degrees). As shown, outside the surrounding region 300, the curvilinear strut segments 116*d* are directly connected to rectilinear strut segments 116*c*. In other words, one end of the curved strut segments 116*d* is connected to the electronic enclosure 160 while the opposing end is connected to a rectilinear strut segments 116*c*. Also as shown, the length of the curvilinear strut segments 116*d* between its opposing connection end points is greater than the length of the rectilinear strut segments 116*c*, respectively. The increased length of the curvilinear strut segments 116*d* as compared to the length of the rectilinear strut segments 116*c* provides for electrical component strain isolation.

As shown in FIG. 21, rather than the strut segments 116 being connected laterally to a vertical side 162 of the enclosure 160, the enclosure 160 (shown by a rectangular dashed line) may be disposed on top of (i.e. raised above/overlie) the curvilinear strain isolation strut segments 116*d* of the base 110/mesh 112, in which case the curvilinear strut segments 116*d* are connected to a bottom side 164 of the enclosure 160.

While particular embodiments of the present invention(s) has/have been described, it should be understood that various changes, adaptations and modifications can be made therein without departing from the spirit of the invention(s) and the scope of the appended claims. Further disclosure regarding the present invention(s) may be found in the publication of Stuart T, Kasper K A, Iwerunmor I C, McGuire D T, Peralta R, Hanna J, Johnson M, Farley M, LaMantia T, Udorvich P, Gutruf P. "Biosymbiotic, personalized, and digitally manufactured wireless devices for indefinite collection of high-fidelity biosignals" Science Advances 2021 Oct. 8; vol. 7(41):eabj3269. doi: 10.1126/sciadv.abj3269. Epub 2021 Oct. 8. PMID: 34623919; PMCID: PMC8500520, hereby incorporated by reference in its entirety. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS

10 body
12 appendage
14 appendage longitudinal direction
16 torso
20 system
30 power caster/transmitted device
40 remote electronic device
42 computer
44 display
100 article
102 energy management (power harvesting) device
104 transmitter and receiver device
110 base
112 mesh
116 strut segment
116*a* cantilevered strut segment
116*b* cantilevered strut segment
116*c* straight (rectilinear) strut segments
116*d* curved (curvilinear) strut segments
120 lattice structure
122 openings
130 end region
132 end region
134 seam
136 head
148 electronic structure
149 electronic component
150 antenna
152 antenna longitudinal direction (sensing article transverse direction)
154 antenna wave shape
156 antenna semi-circular segments
158 sensing article longitudinal (circumferential) direction
160 electronic enclosure
160*a* lower electronic enclosure
160*b* upper electronic enclosure
162 vertical side of enclosure
163 height of the lower enclosure
164 bottom side
166 top side
170 recess (170*a*-170*h*)
176 lower electronic components
180 lower electrical power conductor
184 electrical insulator
188 upper electrical power conductor
188*a* antenna (power receptor) segment
192 upper electronic components
194 power management integrated circuit
195 energy storage device
196 sensors
198 system on a chip
199 microfluidic structure
200 microfluidic channel
202 microfluidic channel longitudinal direction
204 microfluidic channel wave shape
206 microfluidic channel semi-circular segments
210 microfluidic channel enclosure
210*a* lower microfluidic channel enclosure
210*b* upper microfluidic channel enclosure
216 inlet
220 annular rib

226 outlet
270 strain gauge sensor
274 elongated strain element
282 first end conductor
286 second end of conductor
290 leads
296 temperature sensor
300 region
θ angle

What is claimed is:

1. A wearable article, comprising:

a three-dimensionally printed base, wherein the base of the article comprises a three-dimensionally printed mesh which is formed of an elastomeric polymer composition; and wherein the mesh is dimensioned to be wrapped fully around a selected body part; and wherein the mesh is formed of a plurality of strut segments arranged in a lattice structure to form a grid of polygonal shaped window openings; and;

a microfluidic channel coupled to the mesh, the microfluidic channel having an inlet and an outlet disposed at opposite ends of the channel, wherein the microfluidic channel is curved in a form of a serpentine shape; and wherein the serpentine shape is provided by a plurality of 180-degree semi-circular segments.

2. The article of claim 1, wherein the microfluidic channel has a length from the inlet to the outlet in the range of 10-100 mm, and a channel area in a range of 0.2-0.4 $mm^2$.

3. The article of claim 1, wherein the plurality of 180-degree semi-circular segments are of a uniform diameter arranged adjacent one another between the inlet and outlet.

4. The article of claim 1, wherein a surface of the microfluidic channel has a contact angle with sweat from a body when disposed thereon of less than 90 degrees.

5. The article of claim 1, wherein the microfluidic channel has a cross-sectional area in a range of 0.2 to 0.4 square millimeters.

6. The article of claim 1, wherein the elastomeric polymer composition is at least one of a synthetic elastomeric polymer composition and a thermoplastic elastomeric polymer composition.

7. The article of claim 1, wherein the elastomeric polymer composition comprises at least one elastomer, wherein the at least one elastomer is a thermoplastic elastomer.

8. The article of claim 7, wherein the at least one thermoplastic elastomer comprises a thermoplastic urethane elastomer.

9. The article of claim 1, wherein the elastomeric polymer composition has at least one of the following mechanical properties:

a Shore A hardness in a range of 60-100 Shore A as measured by ASTM D2240;

a tensile strength in a range of 2-60 MPa as measured by ASTM D412;

an elongation at break in a range of 400-800% as measured by ASTM D412.

10. The article of claim 1, wherein, when disposed on a body, the mesh is flexible and stretchable as to conform to changes in a shape of the body during movement of the body.

11. The article of claim 1, further comprising:

at least partially embedding at least one electronic component in the base.

12. The article of claim 11, wherein the at least one electronic component comprises at least one sensor to collect data concerning the wearer when the article is worn by the wearer.

13. The article of claim 12, wherein the at least one sensor comprises at least one of a temperature sensor, a strain sensor, an accelerometer and a humidity sensor.

14. The article of claim 11, wherein the at least one electronic component comprises at least one antenna.

15. The article of claim 11, wherein the at least one electronic component comprises a wireless transmitter and receiver.

16. The article of claim 11, wherein the at least one electronic component comprises a data collection component.

17. The article of claim 11, wherein the at least one electronic component comprises an energy harvesting and power management component.

18. The article of claim 11, wherein the at least one electronic component comprises a wireless communication component.

19. The article of claim 1, wherein the article is a component of a system which further comprises a radio-frequency power transmitter.

20. The article of claim 1, wherein the article provides wireless communication and power charging.

21. The article of claim 1, wherein the article is battery-free.

* * * * *